United States Patent
Schryver

(10) Patent No.: US 10,531,656 B2
(45) Date of Patent: Jan. 14, 2020

(54) CRYOGENIC WORKSTATION USING NITROGEN

(71) Applicant: BioLife Solutions, Inc., Bothell, WA (US)

(72) Inventor: Brian Schryver, Redwood City, CA (US)

(73) Assignee: BioLife Solutions, Inc., Bothell, WA (US)

( * ) Notice: Subject to any disclaimer, the term of this patent is extended or adjusted under 35 U.S.C. 154(b) by 1037 days.

(21) Appl. No.: 14/895,488

(22) PCT Filed: Jun. 3, 2014

(86) PCT No.: PCT/US2014/040761
§ 371 (c)(1),
(2) Date: Dec. 2, 2015

(87) PCT Pub. No.: WO2014/197515
PCT Pub. Date: Dec. 11, 2014

(65) Prior Publication Data
US 2016/0143270 A1     May 26, 2016

Related U.S. Application Data

(60) Provisional application No. 61/890,036, filed on Oct. 11, 2013, provisional application No. 61/879,624, (Continued)

(51) Int. Cl.
*F25D 3/10* (2006.01)
*F25B 19/00* (2006.01)
(Continued)

(52) U.S. Cl.
CPC ......... *A01N 1/0257* (2013.01); *F21V 21/096* (2013.01); *F25D 3/10* (2013.01);
(Continued)

(58) Field of Classification Search
CPC . F25D 3/10; F25D 3/102; F25D 3/105; F25D 3/107; F25B 19/00; F17C 13/026;
(Continued)

(56) References Cited

U.S. PATENT DOCUMENTS 3,108,840 A    10/1963  Conrad et al.
3,257,820 A     6/1966  Case et al.
(Continued)

FOREIGN PATENT DOCUMENTS

GB    1518792 A  *  7/1978  ............... F25D 3/10
JP    H1-281383 A    11/1989
(Continued)

OTHER PUBLICATIONS

CN201480038406.7, "Office Action", dated Dec. 23, 2016, with English translation 25 pages.
(Continued)

*Primary Examiner* — Frantz F Jules
*Assistant Examiner* — Erik Mendoza-Wilkenfel
(74) *Attorney, Agent, or Firm* — Kilpatrick Townsend & Stockton LLP

(57) ABSTRACT

Cryogenic devices are provided in which liquid nitrogen is used to maintain ultra-low temperatures in which samples can be manipulated.

35 Claims, 28 Drawing Sheets

Related U.S. Application Data filed on Sep. 18, 2013, provisional application No. 61/873,298, filed on Sep. 3, 2013, provisional application No. 61/860,801, filed on Jul. 31, 2013, provisional application No. 61/830,354, filed on Jun. 3, 2013.

(51) Int. Cl.

| | | |
|---|---|---|
| *F17C 3/02* | (2006.01) | |
| *A01N 1/02* | (2006.01) | |
| *H01S 5/02* | (2006.01) | |
| *F21V 21/096* | (2006.01) | |
| *H01S 5/022* | (2006.01) | |
| *F21Y 115/30* | (2016.01) | |
| *F21Y 115/10* | (2016.01) | |

(52) U.S. Cl.
CPC ........... *H01S 5/022* (2013.01); *F21Y 2115/10* (2016.08); *F21Y 2115/30* (2016.08)

(58) Field of Classification Search
CPC ...... F17C 2250/0408; F17C 2250/0413; F17C 2250/0417; F17C 2250/061; F17C 2227/0121; F17C 2270/0509; A01N 1/0257; F21V 21/096; H01S 5/022; F21Y 2115/10; F21Y 2115/30
See application file for complete search history.

(56) References Cited

U.S. PATENT DOCUMENTS

| | | | |
|---|---|---|---|
| 4,494,415 A | | 1/1985 | Elliston et al. |
| 4,875,340 A | | 10/1989 | Liu et al. |
| 5,048,300 A | | 9/1991 | Lihl et al. |
| 5,080,935 A | * | 1/1992 | Kelso, Jr. .................. B27K 1/00 34/404 |
| 5,309,722 A | * | 5/1994 | Phillips, Jr. ............... F25D 3/10 62/373 |
| 5,410,910 A | | 5/1995 | Siao et al. |
| 5,606,860 A | | 3/1997 | Popp et al. |
| 5,671,603 A | * | 9/1997 | McCorkle ............. F17C 13/021 137/392 |
| 6,065,303 A | | 5/2000 | Harris |
| 6,122,232 A | | 9/2000 | Schell et al. |
| 6,266,306 B1 | | 7/2001 | Schell et al. |
| 6,487,866 B1 | | 12/2002 | Fesmire et al. |
| 2005/0006272 A1 | | 1/2005 | Derifield |
| 2005/0016198 A1 | | 1/2005 | Wowk et al. |
| 2005/0039484 A1 | | 2/2005 | Nielsen |
| 2005/0188715 A1 | | 9/2005 | Aragon et al. |
| 2006/0076385 A1 | * | 4/2006 | Etter ...................... B23B 25/06 227/2 |
| 2006/0218963 A1 | | 10/2006 | Elias |
| 2006/0283197 A1 | | 12/2006 | Schon et al. |
| 2007/0151283 A1 | | 7/2007 | Whewell |
| 2008/0292220 A1 | | 11/2008 | Zacchi |
| 2008/0302119 A1 | | 12/2008 | Shaw |
| 2009/0230139 A1 | | 9/2009 | Li |
| 2012/0102983 A1 | | 5/2012 | Parmegiani et al. |
| 2012/0140413 A1 | | 6/2012 | Rawson et al. |
| 2012/0255313 A1 | | 10/2012 | Katkov et al. |
| 2012/0279896 A1 | | 11/2012 | Lantz |
| 2014/0033759 A1 | * | 2/2014 | Ide ....................... F25D 23/062 62/457.2 |
| 2014/0047851 A1 | | 2/2014 | Zhou |
| 2016/0114326 A1 | | 4/2016 | Schryver et al. |

FOREIGN PATENT DOCUMENTS

| | | | |
|---|---|---|---|
| JP | 2001-24243 A | | 1/2001 |
| JP | 2005021978 A | * | 1/2005 |
| WO | 2012112035 | | 8/2012 |
| WO | 2012112035 A1 | | 8/2012 |
| WO | 2014197511 | | 12/2014 |
| WO | 2014197515 A1 | | 12/2014 |

OTHER PUBLICATIONS

EP14807960.1 , "Extended European Search Report", dated Dec. 19, 2016, 9 pages.
EP14807189.7 , "Extended European Search Report", dated Mar. 24, 2017, 7 pages.
PCT/US2014/040756 , "International Preliminary Report on Patentability", dated Dec. 17, 2015, 13 pages.
PCT/US2014/040761 , "International Preliminary Report on Patentability", dated Dec. 17, 2015, 10 pages.

* cited by examiner

CRYOGENIC WORKSTATION USING NITROGEN

FIELD OF THE INVENTION

The invention relates to open-top workstations for manual and robotic procedures that require low operation temperatures and methods for making and using the same.

RELATED APPLICATIONS

This application is a US National Phase of PCT Application No. PCT/US2014/040761 filed on Jun. 3, 2014, which claims benefit of each of the following U.S. provisional applications: No. 61/830,354 (filed Jun. 3, 2013); No. 61/860,801 (filed Jul. 31, 2013); No. 61/873,298 (filed Sep. 3, 2013); No. 61/879,624 (filed Sep. 18, 2013); and No. 61/890,036 (filed Oct. 11, 2013). The entire content of each of these applications is incorporated herein by reference for all purposes.

BACKGROUND OF THE INVENTION

Many industrial, commercial, and research processes require, for optimal results, that an object or material be maintained at a low temperature. For example, cryogenic preservation or maintenance at low temperature is a common means of insuring the molecular integrity of specimens and products. Substances that would degrade in a relatively short interval at higher temperatures can be stored with limited or no change for long durations at temperatures below the material freezing point. While frozen storage can be effective in decreasing the rate of sample degradation, in aqueous solutions and biological specimens, molecular activity does not cease until a temperature near −130° C. At temperatures above this point, there remains an opportunity for the specimen to re-order the solid structure, thereby creating changes in the specimen that may lead to a decrease in the integrity of the sample. Examples of this type of sample damage include, upon thawing, a decrease in viability of cryogenically stored cells, a reduction of enzymatic activity, and a decrease in the potency of pharmaceuticals.

The opportunity for deleterious changes in frozen specimens increases greatly under conditions where the sample experiences transient fluctuations in temperature such as may occur when stored materials are transferred from one cold storage system to another, or when held inside a storage system that undergoes temperature spikes, such as those introduced when a freezer door is opened for normal access, during intervals of power failure, or even during normal mechanical refrigeration temperature cycles over time.

Despite the need for prevention of temperature spikes and fluctuations in samples, there is often a need for extensive manipulation of samples outside of the normal frozen storage system. For example, cell vials may need to be re-organized, cataloged, or traced, requiring exposure to higher temperatures for time periods of several minutes to one-half of an hour or longer. Other requirements for extended manipulation time outside of freezer storage include preparation of samples for shipping or local transport; receiving, sorting, and storage of sample shipments; and packaging and labeling of frozen products.

SUMMARY OF THE INVENTION

The present invention provides devices that are containers that can maintain a heavier-than-air gas (typically a cold gas) in a well, or "chamber" of the device, wherein a large portion of the chamber depth (from the floor of the device, on which samples or "objects" rest, to the top of the chamber) is at or below a desired temperature limit, and wherein temperature-sensitive object manipulations and operations may be conducted through the open top of the container (the top of the chamber) while maintaining the object temperature within a specified temperature range. A device of the invention is, in one embodiment, a container with one (if circular in shape) or more (i.e., rectangular or square in shape) sides and a bottom constructed from an insulating material, comprising a gas-tight well or chamber in which dense cold gas may be contained.

In one embodiment, the contained gas is nitrogen, and the temperature of the contained gas is held within the desired range by the boiling of liquid nitrogen contained within an open tank (e.g., metal tank) that is mounted to an interior wall of the chamber. The tank is configured in a manner such that nitrogen vapor effluent is exhausted directly into the chamber, thereby mixing the chamber gas and increasing the rate of exposure of the warmer chamber gas to the exposed surface of the boiler, resulting in more uniform and lower gas temperatures in the section of the chamber that holds the samples of interest (from the floor to a height sufficiently above the floor to ensure the samples are completely contained in the heavier-than-air gas).

The invention also provides methods for using the devices to manipulate samples in cold storage as well as additional embodiments of the device that provide for maintaining and monitoring the level of the liquid nitrogen within the tank or the amount of other coolant within the chamber as well as the collection of chamber gas temperature data for the purpose of insuring temperature compliance of the working volume.

Some implementations of the present invention further include a removable laser carriage having a magnetic mounting system. The mounting system comprises compatible electrical terminals or contacts that deliver electrical current to the laser diodes when the laser carriage is coupled to the sensor harness. The mounting system includes a harness adapter that may be permanently coupled to the harness. An opening is provided in the harness and electrical lead wires extend out of the opening and through the harness adapter. A mounting plate is further provided having electrical terminals that attach to the lead wires, observing the polarity of the lead wires. The mounting plate is attached to the harness adapter via a fastener. The electrical terminals of the mounting plate protrude outwardly on a side of the plate that is opposite the harness adapter. The laser carriage further comprises a recess for receiving the mounting plate. The recess includes additional electrical leads that are in alignment with the electrical leads of the mounting plate. In some instances, the mounting plate and recess further comprise complementary magnets, whereby the mounting plate is temporarily or selectively coupled to the recesses via a magnetic interface.

In some embodiments, the laser carriage may comprise two laser diodes. The electrical terminals of the laser carriage are operably connected to the laser diodes via electrical lead wires. When the mounting plate is coupled to, or set into the recess of the laser carriage, electrical current is delivered to the laser diodes via the interface between the electrical terminals and respective lead wires. When desired, the laser carriage may be simply removed from the harness by separating the magnetic connection between the mounting plate and the laser carriage. The fit between the mounting plate and the recess ensure proper, repeatable alignment of the laser diodes within the chamber of the container.

In one aspect, the invention provides a container comprising one or more sides and a floor with an open-top surface forming an interior chamber wherein a liquid-tight metal tank comprising at least one opening at the top surface of the tank capable of exhausting gas directly into the chamber is mounted on or in close proximity to an interior side wall. In some embodiments the container comprises a material with a thermal conductivity less than 0.2 watts per meter kelvin. In some embodiments the material comprises cross-linked polyethylene foam, urethane foam, styrene foam, polyvinyl foam, or a polymer blend foam. In some embodiments the tank metal is composed of or comprises steel, stainless steel, copper, a copper alloy, aluminum, or an aluminum alloy. In some embodiments the tank comprises rim projections to limit spillage of the tank contents. In some embodiments the tank comprises one or more liquid-filling ports, liquid flow control mechanisms, sensor mounts, and sensor housings. In some embodiments the device comprises a liquid level sensor or a temperature sensor or both.

In some embodiments the device comprises a cover or lid that may reduce temperature and liquid nitrogen use, e.g., during periods of inactivity.

In some embodiments the device is attached to piping, tubing or gravity chutes to direct liquid into the tank. In some embodiments the device is attached or operably linked to a microprocessor receiving electric signals from a liquid level sensor or from temperature sensor or both, and delivering an electric signal to a liquid delivery regulator.

In some embodiments the chamber comprises one or more temperature sensors to monitor the interior gas temperature. In some embodiments the the temperature sensor is a thermocouple or an RTD sensor.

In some embodiments the attached external liquid refrigerant reservoir is pressurized by an electric current passed through a resistance coil that is submerged in the liquid, or where the liquid refrigerant is moved through the action of a mechanical pump. In some embodiments the liquid nitrogen delivery system comprises a covered gravity chute.

In some embodiments the tank is positioned in the interior chamber so that the lowest rim of the tank opening is no lower than seventy-five percent of the height of the interior chamber. In some embodiments the tank is positioned in the interior chamber so that the lowest rim of the tank opening is no lower than fifty percent of the height of the interior chamber. In some embodiments the tank is positioned in the interior chamber so that the lowest rim of the tank opening is no lower than eighty percent of the height of the interior chamber. In some embodiments the tank is positioned in the interior chamber so that the lowest rim of the tank opening is no lower than sixty percent of the height of the interior chamber. In some embodiments the the tank has one or more level top edges whereby overflow of cold gas from the tank will fall evenly down the tank face beneath the level edge. In some embodiments the the tank is constructed with a long dimension greater than fifty percent of the length of the chamber wall on which it is affixed. In some embodiments the the tank interior comprises removable or permanently attached baffles, screens, or porous materials that may suppress or restrict liquid movement in the tank interior.

In one aspect the system comprises a device as described hereinabove, and a laser mounting system. In one aspect the invention provides a laser mounting system, comprising: a laser carriage comprising a laser diode electrically connected to a first electrical terminal, and further comprising a first magnet; a mounting plate comprising a second electrical terminal and a second magnet, the second electrical terminal and second magnet being positioned to align with the first electrical terminal and the first magnet when laser carriage is coupled to the mounting plate; a harness adapter having a first surface for receiving an outer surface of a sensor harness and an opposing surface for receiving the mounting plate, the harness adapter being interposed between the harness and the mounting plate; and a lead wire coupled to the second electrical terminal. In some embodiments the laser carriage comprises a pair of laser diodes.

In an embodiment, a front surface of the laser carriage comprises a plane, and wherein a side corner edge of the front surface is angled inwardly in the range of 10°-50°, optionally at approximately 30°, relative to the plane of the front surface, wherein a central axis of the laser diode is angled at approximately 30° relative to the plane of the front surface.

In an embodiment, the laser carriage comprises a first laser diode positioned on a first angled corner of the front surface, and a second laser diode positioned on a second angled corner of the front surface, wherein the first angled corner is opposite the second angled corner on the front surface. In an embodiment, an angle between a central axis of the first laser diode and a central axis of the second laser diode is in the range of 20°-100°, optionally at approximately is approximately 60°.

In an embodiment, the laser carriage is selectively removable from the mounting plate. In an embodiment, the harness adapter is permanently attached to the harness. In an embodiment, the mounting plate is removably coupled to the harness adapter via a fastener. In an embodiment, the laser mounting system comprises a magnetic interface between the mounting plate and the laser carriage. In an embodiment the laser mounting system includes a keyed connection between the mounting plate and the laser carriage.

In one aspect, the invention provides a method for creating a container with an open-top chamber filled with low temperature gas wherein a portion of the gas is at a temperature below −80 degrees Celsius comprising evaporating liquid nitrogen within a metal tank affixed to the container wall and exhausting the nitrogen vapor directly into the container chamber.

In some embodiments the container chamber gas temperature is regulated by control of the level of refrigerant contained within the tank. In some embodiments the nitrogen vapor is exhausted in a manner such that the gas within the container cavity is mixed at an increased rate relative to the rate obtained using liquid nitrogen contained in a pan resting on the floor of the chamber. In some embodiments the uniformity of the gas temperature within the chamber is increased by the mixing effect of the gas effluent from the metal tank.

In some embodiments, the chamber gas temperature is regulated by control of the level of refrigerant contained within the tank.

In some embodiments, the nitrogen vapor is exhausted in a manner such that the gas within the container cavity is mixed at an increased rate relative to the rate obtained using liquid nitrogen contained in the same tank when resting on the floor of the chamber.

In some embodiments, the uniformity of the gas temperature within the chamber is increased by the mixing effect of the gas effluent from the metal tank.

In some embodiments, the chamber temperature is at a reduced temperature compared to the same tank when resting on the chamber floor.

In some embodiments, the gas flow from the boiler increases exposure of the warmer cavity gas to the liquid nitrogen surface.

In some embodiments, the visual clarity of the working space within the chamber is improved by ejection of gas-suspended solidified water vapor by gas within the chamber cavity overflowing the chamber rim relative to the clarity obtained using liquid nitrogen contained in the same tank when resting on the floor of the chamber.

In some embodiments, the exposure of the gas content of the chamber to the boiler is increased by the momentum of the gas effluent from the boiler falling in a gravitational field.

In one aspect the invention provides a method for creating an extended open-top chamber by removing a portion of one or more side-walls and joining the containers to form a continuous interior chamber wherein a liquid-tight metal tank comprising at least one opening at the top surface of the tank capable of exhausting gas directly into the chamber is mounted on or in close proximity to an interior side wall.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Figure 1:
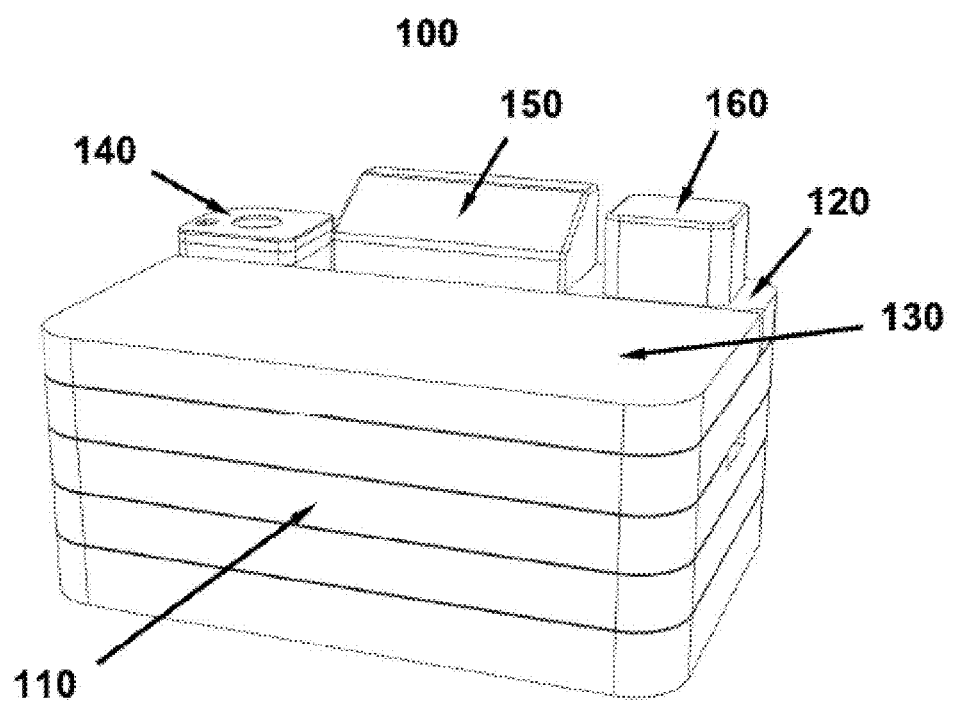
FIG. 1 shows a line drawing of an embodiment of a device of the invention illustrating external components of the device.

The present invention provides open-container systems comprising a well chamber of cold gas in which temperatures comparable to freezer interior temperatures can be maintained for the purpose of manipulating temperature-sensitive materials. In such an open system, a leak-free insulated container retains cold gas, as the greater density of the cold gas compared to the warmer atmosphere gas temperature restricts movement past the container rim. While the contained gas can increase in temperature and decrease in density during operation, allowing the opportunity for the gas to escape, environmental heat that enters the container system through the insulated walls and floor of the container and primarily through the atmospheric gas and cold gas interface can be absorbed by the system through the latent heat of vaporization by a phase change material, such as liquid nitrogen, within the chamber.

The present invention offers significant advantages over mechanical refrigeration systems, as the thermal burden placed on mechanical refrigeration systems to hold low temperatures in the range of −130° C. to −80° C. in an open system makes them impractical for this application for extended work periods. Phase-change materials, when introduced into the chamber at the appropriate supply rates, can have sufficient latent heat absorption capacity to maintain the necessary temperature range. Liquid nitrogen, with a boiling temperature of −196° C. at atmospheric pressure, has the capacity to hold open system containers in the range of approximately −150° C. and higher.

Phase change materials when used as open system coolants present limitations that may be problematic for the temperature range required and the working space available when placed directly on or near the bottom surface of the chamber. As heat enters the system from the open top, a temperature gradient develops between the atmospheric temperature at the container rim and the phase change material temperature inside the container. The temperature gradient may place a substantial zone of the container volume outside of the necessary temperature range for the desired procedure. For example, if samples stored in a −80° C. mechanical freezer need to be cataloged and sorted into different containers before being returned to storage, a working temperature zone of less than −80° C. will be required to prevent a temperature increase in the samples. A temperature gradient may otherwise place a portion of the sample above the desired temperature range, thereby subjecting the sample to a fault condition.

The devices of the present invention overcome such problems and provide an open system that can be used to manipulate materials in a frozen state while maintaining them in that frozen state, but enable the people or equipment performing such manipulations to be in a warmer environment. In various embodiments, the devices are mobile.

Materials that are being stored in a frozen state at low temperatures (−130° C. to −80° C.) often require additional operations such as sorting, inventory, transfer, boxing, labeling, cataloging, and location confirmation. Such operations typically require time intervals, spatial volumes, and access orientations that prohibit the performance of these operations inside the frozen storage housing. For such operations, an open-top container wherein the interior temperature is at or below the long-term storage temperature is appropriate for optimal preservation of sample integrity. The size of a container for operations of this nature can range from, for example and without limitation, an area of 5 inches to 96 inches in length, 5 inches to 36 inches in width, and 5 inches to 24 inches in depth.

Creating an open and portable well of cold gas in the range of −130° C. to −80° C. precludes, for most purposes, the use of mechanical refrigeration systems, as the degree of heat influx exceeds the capacity of such systems due to the power requirements, in addition to the limitations imposed by the physical size and mass of the systems required for extended duty cycles. A phase change material such as liquid nitrogen allows an open loop refrigeration system to be applied wherein thermal energy is removed in a relaxed time frame from the refrigerant at a remote site (e.g., an air liquifaction plant) and, at a later time, the warmed refrigerant (nitrogen gas) is ejected from the system to the atmosphere, rather than returned to a condenser as is done with conventional refrigeration systems. As a result, greatly concentrated cooling power can be applied to a relatively small volume without the need for localized mechanical elements. A system wherein the liquid nitrogen phase change from liquid to gaseous state takes place inside the chamber is the most efficient design as the heat absorbing capacity of the latent heat of vaporization will provide an excellent sink for the thermal energy influx from the surrounding environment. Therefore, in one embodiment of a device of the invention, an independent tank or pool of liquid nitrogen inside the working chamber offers a simple and practical solution that can also satisfy a mobility requirement for the system.

While a container of liquid nitrogen resting on the floor of the chamber is an effective means of holding the temperature to the desired range within a shallow depth, under equilibrium operation conditions, a temperature gradient between the environmental temperature at a close proximity above the chamber rim extending to the container floor temperature is established. The temperature gradient can place a substantial portion of the chamber volume in a temperature range that is outside of the specified upper limit. In addition, as the liquid nitrogen is consumed, the temperature at any given level inside the chamber rises accordingly, which may also expose materials inside the chamber to temperatures above the specification limit.

Although active mixing of the cold gas in an open-top refrigeration system can homogenize the gas temperature in the chamber, the turbulence associated with active mixing of the gas will, at the container surface, entrain atmospheric gas into the mixture, thereby introducing both environmental heat and atmospheric water vapor into the cold chamber. The instant invention comprises a liquid nitrogen expansion system, in the form of a linear boiler that exhausts the gaseous nitrogen into the working chamber in a manner that provides a controlled, symmetric, directed and gentle mixing action to homogenize and reduce the chamber gas temperature while producing a gas shield effluent from the chamber that reduces both environmental heat and water vapor influx to the working chamber.

The gentle mixing of the chamber gas and the nitrogen gas vapor further serves to increase the rate of exposure of the chamber gas to the boiler exterior, thereby allowing the liquid nitrogen to absorb the heat more efficiently, resulting in a lowering of the chamber gas temperature.

In some embodiments, the side of the tank that is mounted to the chamber wall (the rear tank wall) is raised above the height of the front tank wall to provide a barrier and return path for liquid nitrogen that has been disturbed by lateral movement of the assembly, and to provide a region of the tank to be used for mounting purposes. (See FIGS. 2, 3 and 4). In some embodiments, the raised rear wall of the tank is used in mounting a guard cover for the tank that for safety, prevents inappropriate placement of hands and fingers inside the boiler interior. As unrestricted nitrogen effluent from the boiler is critical to the proper function of the boiler, a guard cover will be suspended above the front rim so as to not restrict the gas flow or increase the gas exit velocity.

The gas in the upper chamber region flowing rearward at the rim level of the chamber will, through interaction with the atmospheric air layer, be at a warmer temperature and lower density than the remainder of the gas within the chamber. As the gas contacts the surface of the linear boiler, thermal energy will be transferred from the gas through the reservoir wall to the liquid nitrogen, thereby cooling the chamber gas and increasing the gas density. The lower density gas will fall downward, displacing the chamber gas and promoting a slow circulation of the chamber gas. As the liquid nitrogen absorbs the thermal energy, the liquid will phase change to gas that is at the lowest gas temperature in the chamber. As the cold and dense gas overflows the front rim of the reservoir, the high density of the gas will mix with the chamber gas, flow past the boiler exterior surface and transfer thermal energy to the liquid nitrogen through the boiler wall, then fall in a curtain to the chamber floor, thereby promoting chamber gas circulation. This continuous gas circulation pattern mixes the chamber gas producing a more uniform temperature while decreasing the overall gas temperature. As the exterior surface of the boiler tank that is directly adjacent to the liquid nitrogen phase inside the boiler tank will be near in temperature to the atmospheric pressure phase change temperature of the liquid nitrogen, the tank exterior surface in this region will be the greatest region of heat exchange with the interior gas of the working chamber. The greater the liquid volume within the boiler, the greater the surface area of the tank that is at or near the liquid nitrogen phase change temperature of −196 degrees C., and as a result of the increased heat exchange, the lower the gas temperature within the chamber. When the boiler of the instant invention described below in FIGS. 2-4, 6A, 6B, 7, and 8 is filled to near maximum capacity, the chamber temperatures within the chamber of the device described in FIGS. 1 and 2 can achieve temperatures below −130 degrees C. Although numerous applications can derive maximum benefit from working chamber temperatures that are in the lowest possible range, for other applications, a restricted temperature range may be required. For example, various pharmaceutical vessels with synthetic lid seals can fail at temperatures below the rated limit while the vial contents cannot be exposed to temperatures above a set limit without degradation. For such applications, the refrigeration capacity of the liquid nitrogen boiler must be under active regulatory control. As the temperature of the working chamber is a function of the magnitude of the exterior surface area of the boiler tank that directly opposes the interior boiler surface area that is in direct contact with the liquid nitrogen phase within the tank interior, the chamber gas temperature can be regulated and controlled by adjustment of the liquid nitrogen volume within the tank. Therefore, through control of the liquid nitrogen level within the boiler tank, the chamber gas temperature can be controlled. In some embodiments, the boiler tank liquid nitrogen level is actively regulated by a microprocessor. In some embodiments, the microprocessor receives a liquid level signal from a sensor and upon the basis of the liquid level data regulates the liquid level within the boiler tank. In some embodiments the microprocessor regulates the liquid nitrogen level upon the basis of thermometric data indicating the chamber gas temperature, while in other embodiments the microprocessor regulates the liquid nitrogen level on the basis of both the chamber gas temperature and the liquid nitrogen level.

In some embodiments, the liquid nitrogen boiler tank is equipped with a float level sensor, while in other embodiments, the level sensor comprises a capacitive sensor, ultrasonic sensor, or thermal sensor.

In some embodiments, the gas chamber temperature is monitored by a single sensor, while in other embodiments, the gas chamber temperature is monitored by multiple sensors.

In some embodiments, liquid nitrogen is delivered to the boiler tank manually, while in other embodiments, the liquid nitrogen is introduced into the boiler tank by an automated delivery system. In some embodiments, the liquid nitrogen feed is delivered through a piping, hose, or gravity chute system from a pressurized vessel while in other embodiments the liquid nitrogen is delivered by a combination of pumping mechanisms and gravity feed.

As the chamber temperature is functionally related to the surface area of the boiler tank, increasing the surface area of the tank through means of coupling the tank to a material with a high thermal conductivity will influence the heat exchange rate with the chamber gas and therefore influence the temperature of the chamber gas. Increasing the surface area of the thermally conductive material that is in thermal contact with the boiler tank will increase the efficiency of the heat exchange with the chamber gas and thereby further lower the chamber gas temperature. Therefore, in some embodiments, the tank is mounted to a heat exchanger, such as, but not limited to, a plate comprising a metal with an array of fin projections.

Figure 8:
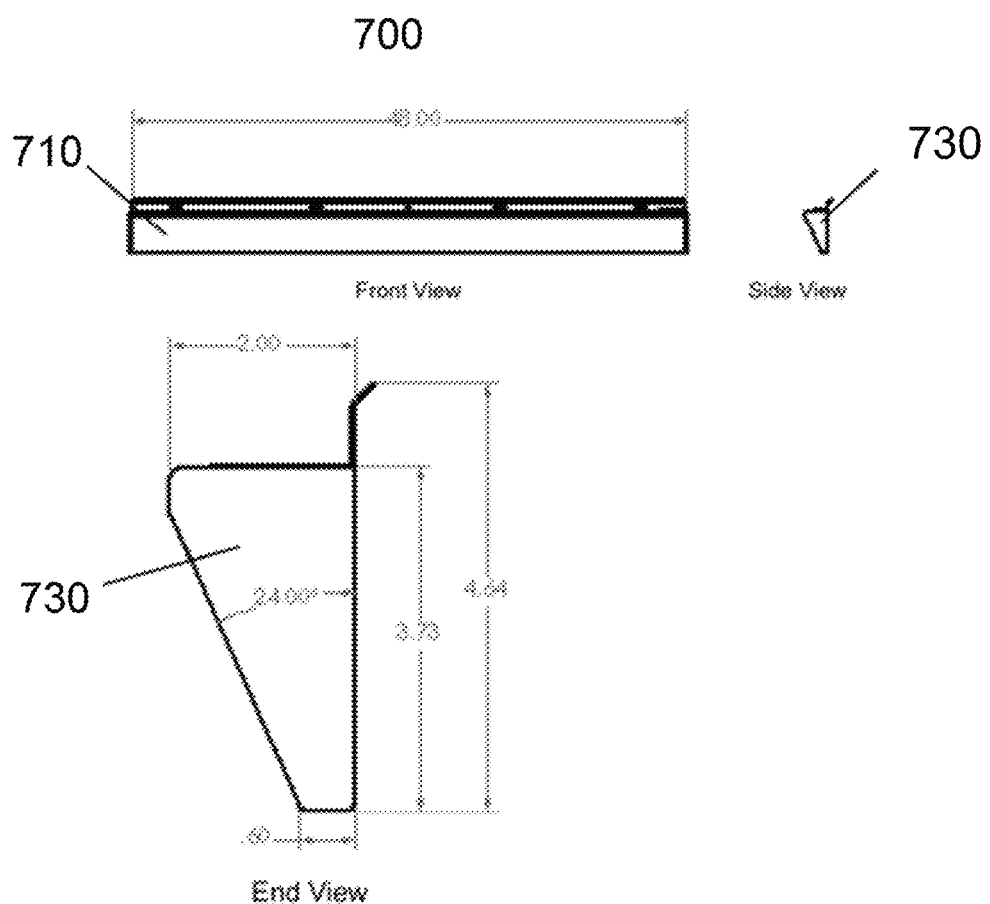
FIG. 8 shows exemplary dimensions of the device shown in FIG. 7.

Due to the greater rate of heat exchange between the chamber gas and the surface of the tank that is adjacent to the liquid phase inside the tank, the cross section geometry of the linear boiler tank will have an influence on the performance of the boiler over a range of fill levels. For example, a rectangular cross-section boiler with a larger height to width ratio will, under operation conditions, experience a more rapid fall in the nitrogen level, a more rapid change in temperature as a function of liquid height, and a greater dynamic temperature operating range than would a rectangular boiler with the same cross-section area and a lower height to width ratio. In the extreme, a rectangular cross-section tank that is tall and narrow will have a good dynamic temperature range but have a rapid rate of fall in liquid level and with concomitant rate of increased in chamber temperature over time, while a tank with a broad and short cross-section will experience a relatively slow decrease in liquid level and shallow increase in chamber temperature over time, but will have a relatively poor dynamic range. As the rate of heat influx into the chamber will be proportional to the difference in temperature between the environment and the lower chamber temperature, operating the chamber at lower temperatures will require a greater rate of phase conversion of the liquid nitrogen and therefore will consume the refrigerant at a greater rate than at higher operation temperatures. As the external surface area of the boiler adjacent to the liquid refrigerant inside increases with refrigerant depth and as a greater external surface area adjacent to the liquid refrigerant is proportional to the rate of heat exchange and therefore to the temperature of the chamber, the greater the level of refrigerant in the boiler, the greater the rate of phase conversion. To hold the chamber temperature to a constant setting, the depth of the refrigerant in the boiler may be maintained at the appropriate level. Therefore the introduction of liquid nitrogen into the boiler at a rate that is equal to the rate of consumption would provide a steady temperature within the chamber providing the rate of heat influx does not change. Regulation of the boiler depth may be achieved by various filling modes, such as: (i) In some embodiments, a constant liquid nitrogen flow rate into the boiler is achieved by means of a proportional valve regulating a constant-pressure liquid nitrogen feed line. In some embodiments a constant pressure feed of liquid nitrogen is provided by a regulated pressurized reservoir while in other embodiments, a constant-pressure liquid nitrogen feed is provided by means of a pumping system that creates a constant head pressure on the feed line. (ii) Alternatively the chamber may be held to a specified range of temperature through which the immediate temperature fluctuates in a regular cycle. A temperature cycling condition may be achieved by an intermittent filling of the boiler to a specified level, followed by an interruption of the liquid nitrogen flow and a repeated fill cycle when the liquid nitrogen level in the boiler is at a minimum specified level. Therefore in some embodiments, the liquid nitrogen flow is regulated by opening and closing of a non-proportional valve gate such as, but not limited to, a solenoid-actuated valve. When operating in the second filling mode, the range of the cycling temperature values may be reduced by an increase in the frequency of the filling cycle. To reduce the requirement for frequent valve actuation in the second mode, it is desirable that the level of the liquid nitrogen within the boiler, change as little as possible with refrigerant consumption. This conditional requirement would best be fulfilled by a boiler cross-section that has a greater width, however as a greater width in a rectangular cross-section boiler also limits the dynamic temperature range that may be achieved by the boiler, the optimal cross-section for a boiler would be a wedge shape wherein the width of the boiler increases with depth. In some embodiments of the invention the tank cross-section profile includes a wedge or triangular element only, while in other embodiments the cross-section is a combination of wedge or triangular elements combined with rectangular elements as shown in FIG. 8.

In some embodiments, the tank is elevated by other means than direct attachment to the chamber wall, such as by a support device. In some embodiments, the support device holds the tank at a fixed elevation, while in other embodiments, the support device can provide a variable height for the tank.

In some embodiments, a single tank is contained within the chamber, while in other embodiments, multiple tanks are contained within the chamber. In some embodiments, multiple tanks are mounted to or positioned on a single wall, while in other embodiments, the tanks are mounted or positioned at more than one wall of the container.

In some embodiments, the front wall of the tank is projected rearward at the top edge to assist in the return of the liquid nitrogen to the tank, to prevent spillage into the chamber under conditions where the assembly is being moved, and to provide structural rigidity to the boiler. In other embodiments, the tank comprises horizontal flanges on the upper side edge of the tank to both suppress spillage in the event of assembly movement and to support additional tank accessories.

In some embodiments, the tank accessories comprise filling ports and funnels to introduce liquid nitrogen into the tank. In other embodiments, the tank accessories comprise level sensor mounts and shields. In other embodiments, the tank accessories comprise baffle plates or other obstructions to induce turbulent fluid flow to prevent or reduce sloshing and spillage of the liquid nitrogen. In other embodiments, the baffle plates comprise horizontal flanges for the purpose of forming barriers to accidental insertion of hands or fingers into the liquid nitrogen.

In some embodiments, the tank comprises a metal. In various embodiments, the metal is or comprises, for example and without limitation, steel, stainless steel, aluminum, aluminum alloy, copper or copper alloy.

In the devices of the invention, the gas chamber comprises one or more walls and a bottom or "floor" that form a gas-tight well. In various embodiments, the chamber wall(s) and bottom are composed of or comprise (as in a layer) an insulating material with a thermal conductivity below 0.2 watts per meter kelvin. In some embodiments, the insulating material is a cross-linked polyethylene foam. In some embodiments, the insulating material is a urethane foam, a plastic-covered urethane foam, a styrene foam, a plastic-covered styrene foam, a polyvinyl foam, or a blended polymer foam (including blends of any of the preceding materials as well as plastic-skinned blends). In some embodiments, the gas chamber is constructed from an inner and outer shell of one material with an interior filling between the inner and outer shell comprising one or more of the above materials. In some embodiments, the shell material comprises a foam material while in other embodiments, the shell material is a solid material.

In some embodiments, the device comprises thermal sensors mounted at one or more locations throughout the chamber interior. In some embodiments, the thermal sensors are thermocouple sensors, while in other embodiments the thermal sensors are RTD sensors.

In some embodiments the gas container comprises a lid to reduce temperature and liquid nitrogen use during periods of inactivity. In other embodiments, the gas container has a rear deck to thermally shield and/or support instrument panels, circuit boards, drying fans, lights, filling ports, data and power linkages, temperature sensor electronics, and data recorders.

In some embodiments the electronic control elements are isolated in an exterior housing attached to the rear exterior surface while in other embodiments the electronic control elements are contained within housings that are remote from the insulated gas container.

When boiling liquid nitrogen is used in the tank, the temperature ranges maintained in the cooling zone of the container will generally range from −196° C. (the boiling temperature of liquid nitrogen at atmospheric pressure) and higher, with a typical performance range of −150° C. to −80° C. (or higher). The "cooling zone" is that region of the container in which the samples or objects to be maintained in a cool state are kept during manipulation. In some embodiments, this cooling zone is identified by use of lines or coloration to delineate it from the upper regions of the container that may be outside the desired temperature range. In other embodiments, the cooling zone limits are identified by horizontal laser beam fan projections. The size of the cooling zone will depend on the size of the chamber, the size of the liquid nitrogen boiler tank, the distance between the bottom of the liquid nitrogen boiler tank and its upper opening from the floor of the chamber, and the amount of liquid nitrogen (or other coolant) in the tank. In some embodiments, a fan laser beam is installed to project a horizontal plane indicator of where the upper working range of the chamber is located.

In one aspect the chamber temperature may be regulated to a temperature within a predetermined temperature range. For example, the chamber temperature measured at the geometric center of the chamber floor at a height half-way between the floor and top chamber opening may be regulated to a temperature within a predetermined temperature range. In this specific context the chamber opening may refer to the opening that is blocked by a chamber cover when such cover is in place. Without limitation, in various embodiments, the temperature range may be, in degrees Celsius, −180 to −50; −100 to −50; −80 to −60, or −80 to −50.

While liquid nitrogen will be the coolant used in the tank for many applications, other coolants can be employed for particular applications. Generally, the coolant will be a liquid or solid that produces a gas more dense than the atmosphere (which may be air but could be any gas or combination thereof and which may be at normal atmospheric pressure but may be at higher or lower pressures) in which the samples or objects are maintained. In some embodiments, other coolants may be used such as and without limitation liquid air, and liquid argon with a boiling point of −186° C. which may be used to create an inert atmosphere. In some embodiments, a gas with a higher molecular weight than nitrogen, oxygen or argon, such as sulfur hexafluoride can be used to fill a portion of the chamber. In such applications, the cold nitrogen gas would form a layer over the dense filler gas, thereby reducing the temperature of and inverting the temperature gradient in the gas layer below the interface.

In addition to the chamber gas circulation properties of the boiler design, the release of nitrogen gas to the chamber interior has the added advantage of enhancing visibility within the chamber. Atmospheric gas contains a percentage of water vapor that upon contact with a cold surface or gas will condense, and if in contact with sub-zero degree Celsius surface or gas will precipitate as a solid. On a surface with a temperature that is below zero degrees Celsius, a solid precipitate can be observed as a growing layer of frost. Over time the thickness of this frost layer of ice crystals can become extensive. In contact with a cold gas layer, however, the atmospheric moisture will precipitate as a fine crystal dust that will fall in a gravitational field and accumulate as an ice dust layer on surfaces below. This layer with time can accumulate depth and become problematic for many processes. In the instant invention, as the nitrogen liquid undergoes a phase change to gas, it expands approximately seven hundred-fold, thereby creating a constant effluent of cold gas that overflows the container rim. The lateral motion of the gas at the surface serves to flush the crystalline water condensate over the container side before it has a chance to settle to the floor of the chamber, thereby significantly reducing both the suspended crystal density as well as the accumulation rate of the ice dust on the floor of the chamber. As the suspended ice crystals scatter light and present a visual impediment, a reduction in the suspended crystal density serves to greatly enhance visibility within the chamber.

Figure 2:
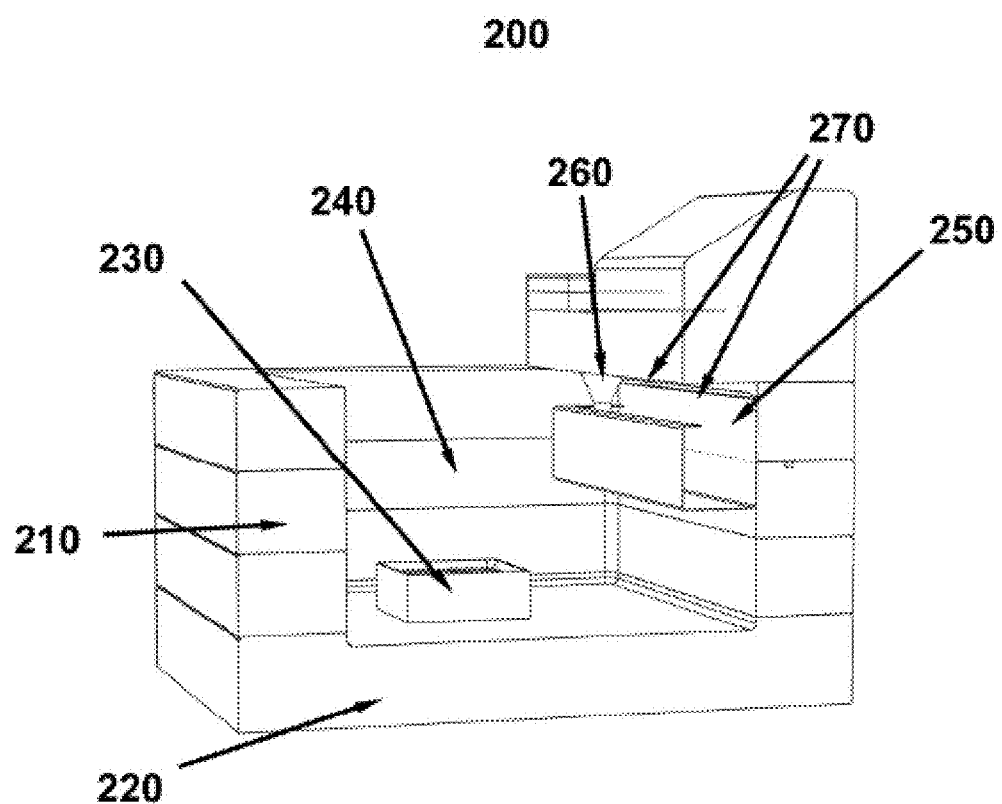
FIG. 2 shows a cross section of the device shown in FIG. 1 revealing internal features of the device.

The ice crystal dust shielding capacity of the instant invention can be estimated for the embodiment shown in FIGS. 1 and 2. The embodiment has in interior volume of 67 liters. With a measured liquid nitrogen consumption rate of 50 cubic centimeters per minute, with an expansion ratio of 696 in the conversion of liquid nitrogen to gas phase, a volume of 34,800 cubic centimeters of nitrogen gas escapes the chamber every minute. With a chamber surface area of 2787 square centimeters, the nitrogen gas release is equivalent to a vertical column of gas rising at a rate of 12.5 centimeters per minute or 4.9 inches per minute. The nitrogen gas upwelling at this rate serves to effectively flush the ice crystal dust suspension that forms at the atmospheric gas-nitrogen gas interface thereby providing the dual benefit of enhanced visibility and substantial reduction in ice crystal dust accumulation. The ice crystal ejection process is readily visible by directing a light source at a low angle onto the nitrogen gas surface at the rim of the invention chamber during operation.

The present invention is not limited by the type or nature of the sample or object placed into the device for maintenance at a desired temperature. For some applications, the device will be used to maintain a biological material in a container at a desired temperature range. For example, the biological material may be or comprise a nucleic acid (e.g. RNA or DNA or modified versions thereof), a protein (e.g. antibodies, chemokines, cytokines, enzymes, hormones, and lymphokines), a lipid (e.g. biological membranes), a virus (e.g. a vaccine), a cell (e.g. primary cell or stem cell or cell lines), bodily tissues and fluids (e.g. blood and blood products, including serum, biopsy materials), and foodstuffs. In various embodiments, the biological material is useful in the treatment or prevention of a disease; such biological materials include nucleic acid-based or protein-based drugs or vaccines. For example, certain envelope viruses useful as vaccines are exceptionally susceptible to degradation at higher temperatures, and the devices of the invention can be used to maintain them at temperatures that maximize stability.

For some applications, the device will be used to maintain an organic or inorganic compound in a container at a desired temperature range. For example, the organic compound can be a drug that is sensitive to temperature fluctuation, and illustrative inorganic materials include materials used in semiconductor chip manufacturing and aerospace engineering and catalysts.

Thus, the invention has wide application, including in the manufacturing and production of aerospace materials, computers, cosmetics, drugs, food, semiconductors, advanced material research, and temperature-sensitive materials generally. The invention will find application in the labeling and packaging of temperature-sensitive materials such as biologics, cells used in stem cell and other therapies, cells used for the production of other products, compounds, drugs, enzymes, and vaccines. The invention will find application in the storage or performance of biological assays. The invention will find application in the transfer of biological and non-biological materials from one container to another, including automated transfers handled manually or by robotics. The invention will find application in the transfer of chilled or frozen or temperature-sensitive materials to cryotanks and liquid nitrogen tanks for long-term storage, as occurs, for example and without limitation, in biobanking, biorepository storage, cryogenic storage, and cryogenics. The invention will also find application in high-through put screening, as in screens conducted for diagnostic purposes and drug discovery. The invention will also find application in welding of materials.

FIG. 1 shows the exterior of an embodiment of an illustrative device of the invention 100. In this embodiment, a container 110 that comprises an insulating foam material is shown with an optional front cover 130. The front cover joins with the back cover or deck 120 that supports the liquid nitrogen fill port 140, the instrument panel 150, and the level detector 160.

Container 110 may comprise any desired exterior dimensions that are compatible with the teachings of the present invention. In some instances, container 110 comprises an outer length from approximately 24.0 inches to 120.0 inches, or greater, from approximately 36.0 inches to approximately 96.0 inches, and in one embodiment an outer length of 66.0 inches. In another embodiment, container 110 comprises an outer length of 35.0 inches.

Container 110 further comprises an outer depth from approximately 12.0 inches to approximately 40.0 inches, from approximately 18.0 inches to approximately 32.0 inches, and in one embodiment an outer depth of 28.0 inches. In another embodiment, container 110 comprises an outer depth of 24 inches.

In some instances, container 110 comprises an exterior height from approximately 6.0 inches to approximately 32.0 inches, from approximately 12.0 inches to approximately 28.0 inches, and in one embodiment an exterior height of 15.0 inches. In another embodiment, container 110 comprises an exterior height of 26.5 inches.

Container 110 may further comprise any interior dimensions that are compatible with the teachings of the present invention. In some instances, container 110 comprises an inner length from approximately 20.0 inches to 116.0 inches, or greater, from approximately 32.0 inches to approximately 92.0 inches, and in one embodiment an inner length of 54.0 inches. In another embodiment, container 110 comprises an inner length of 27.0 inches.

Container 110 further comprises an inner depth from approximately 8.0 inches to approximately 36.0 inches, from approximately 14.0 inches to approximately 28.0 inches, and in one embodiment an inner depth of 16.0 inches.

In some instances, container 110 further comprises an interior height from approximately 6.0 inches to approximately 24 inches, from approximately 8.0 inches to approximately 22.5 inches, and in one embodiment an interior height of 10 inches. In another embodiment, container 110 comprises an interior height of 9.5 inches. In yet another embodiment, container 110 comprises an interior height of 21.5 inches.

Container 110 further comprises a wall thickness that is selected to optimize the insulative properties of the device. In some instances, container 110 comprises a wall thickness from approximately 2.0 inches to approximately 12.0 inches, from approximately 8.0 inches to approximately 10.0 inches, and in one embodiments a wall thickness of 6.0 inches.

Container 110 may further comprise a front cover or lid 130 having a thickness selected to optimize the insulative properties of the device. In some instances, lid 130 comprises a thickness from approximately 1 inch to approximately 2 inches, and in one embodiments a thickness of 2.5 inches. Container may further comprise a bottom or base 122 having a thickness selected to optimize the insulative properties of the device. For example, in some instances base 122 comprises a thickness from approximately 2 inches to approximately 8 inches, from approximately 2.5 inches to 4 inches, and in one embodiment a thickness of 3.5 inches. Lid 130 may further comprise a notch (not shown) to permit passage or cords and other circuitry of the device.

Container 110 may be constructed from a single, monolithic material or from a lamination of a plurality of individual pieces. In some instances, container 110 comprises a lamination of two or more sections. In one embodiment, container 110 comprises a lamination of three middle sections 124 coupled to a base 122 and configured to receive a lid 130. Middle sections 124 may each comprise an individual thickness that provides a desired inner height following lamination. For example, in some instances each middle section 124 comprises an individual thickness from approximately 2 inches to approximately 6 inches, from approximately 2.5 inches to 4 inches, and in one embodiment an individual thickness of 3.25 inches. In another embodiment, each middle section 124 has an individual thickness of 3.0 inches.

The overall dimensions of the embodiment shown are 35 inches in length by 24 inches in width and 15.5 inches in height at the top surface of the cover. The interior chamber dimensions measure 27 inches in length by 16 inches in width by 9.5 inches in depth.

Now referring to FIG. 2, a cross section of the embodiment shown in FIG. 1 200 is presented. The container bottom 220 is joined to the container walls 210 to form a gas-tight open chamber 240 into which the samples to be manipulated 230 are placed. The liquid nitrogen is contained in an open tank assembly 250 that is mounted to the back wall of the container 210 with a series of fasteners 270. A fill port 260 is fixed under a liquid nitrogen passage way in the top cover deck. On the opposite end of the tank (not shown) is a float sensor to monitor the liquid nitrogen level. Under operating conditions, the liquid nitrogen contained within the tank boils, thereby absorbing heat through the tank walls and floor as well as from the warmer gas to which the liquid surface is exposed as the gas moves downward along the inside back wall of the tank. The cold and dense nitrogen vapor released by the boiling liquid overflows the front of the tank and cascades downward in a curtain of dense gas to fill the lower portion of the chamber 240, displacing the chamber gas forward along the chamber floor. The displaced gas rises along the front side of the chamber as it mixes with the warmer air in the mid and upper region of the chamber, and is then carried rearward toward the tank where the flow pattern repeats continuously. The gas flow disturbs and mixes the gas that would otherwise form a temperature gradient and by the mixing creates a more uniform temperature inside the chamber. The elevation of the tank 250 is critical to the proper function of the device. If tank is positioned at or near the floor of the interior chamber, the liquid nitrogen gas effluent overflowing the boiler tank would by virtue of the higher density spread across the chamber floor and as the gas absorbs thermal energy and expands, will be lifted by the evolving colder gas effluent from the tank. As a result the chamber will be filled with a rising column of gas with a temperature gradient decreasing from the warmest gas at the chamber surface to the newly evolved gas at the floor of the chamber. When mounted at an elevation on the interior wall, the overflowing dense gas gains downward velocity and momentum as it falls in the gravitational field. Upon reaching the chamber floor, the momentum of the gas carries it forward toward the opposite interior wall of the chamber interior, thereby inducing a chamber gas circulation pattern of a horizontal roll with an axis that is parallel to the lower rim of the boiler tank. The interior gas circulation pattern is continuously fed by the boiler effluent while the cold gas phase is overflowing the tank. By this gentle rolling motion, the interior gas is continuously mixed, thereby providing a more uniform temperature within the interior chamber. To achieve this effect, in some embodiments, the tank rim (shown below in FIG. 3, element 320) is placed at an elevation above the chamber floor no less than seventy-five percent of the height of the interior chamber wall. Other placements are possible depending on the configuration of the chamber (including, for example, the present or absence of a collar or chimney structure at the top opening). In other embodiments, the location of the tank rim may be selected to provide the desired working depth at the selected temperature range while the overall depth of the of the chamber above the boiler rim may be increased to enhance the gas insulation layer above the working zone, thereby decreasing the rate of environmental heat influx. The benefit of the elevated tank in lowering the interior gas temperature and creating a more uniform chamber gas temperature is demonstrated below in FIG. 5. If the chamber gas is disturbed by turbulent flow the likelihood of entraining atmospheric gas is increased. If the gas effluent from the boiler is uneven, then the gas mixing could become non-uniform, therefore optimum performance of the boiler will be obtained when the boiler is configured such that the dense gas overflows the boiler in an even curtain than extends the length of the chamber interior. To achieve an even cascade of cold gas, the optimal placement of the front rim of the linear boiler will be in a level orientation.

Figure 3:
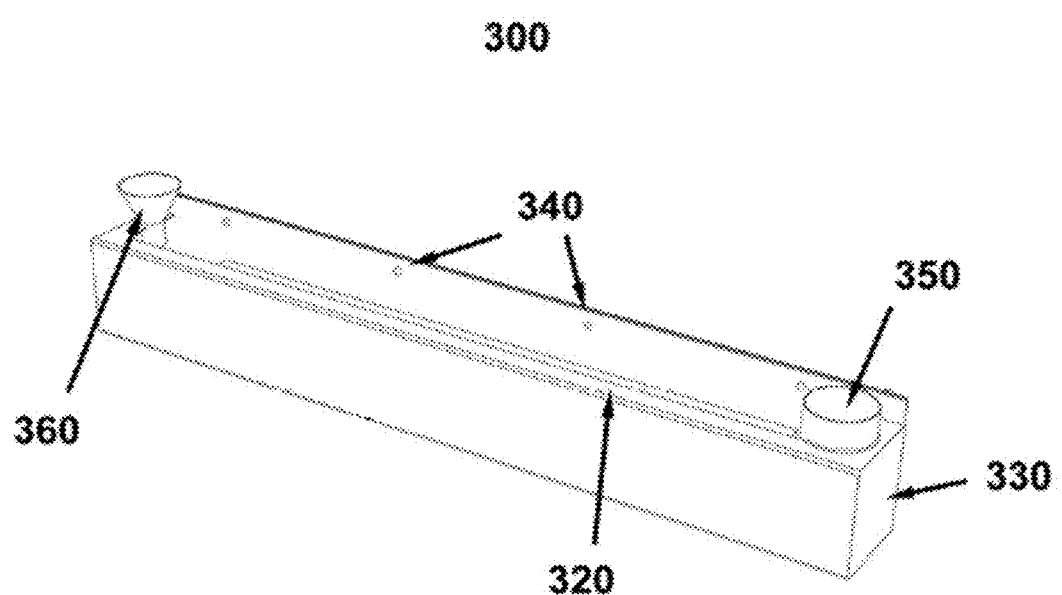
FIG. 3 shows a line drawing of a liquid nitrogen gas circulation boiler for use in a device of the invention.

Now referring to FIG. 3, the entire length of the tank 300 described in FIG. 2 is shown. The tank comprises a length of a metal trough that is enclosed on the ends by endplates 330 to form a liquid-tight tank. The front rim of the tank 320 extends horizontally to the rear to return splashed liquid to the tank. The rear wall of the tank is mounted to the container wall by screws introduced through mounting holes 340. A float sensor housing 350 receives the float mechanism for liquid nitrogen level sensing and also acts as a surge suppressor when the assembly is in motion. The dimensions of the tanks shown measure 26 inches in length, 3 inches in width, and 3.25 inches in height at the front side and 4.25 inches in height on the rear side.

Figure 4:
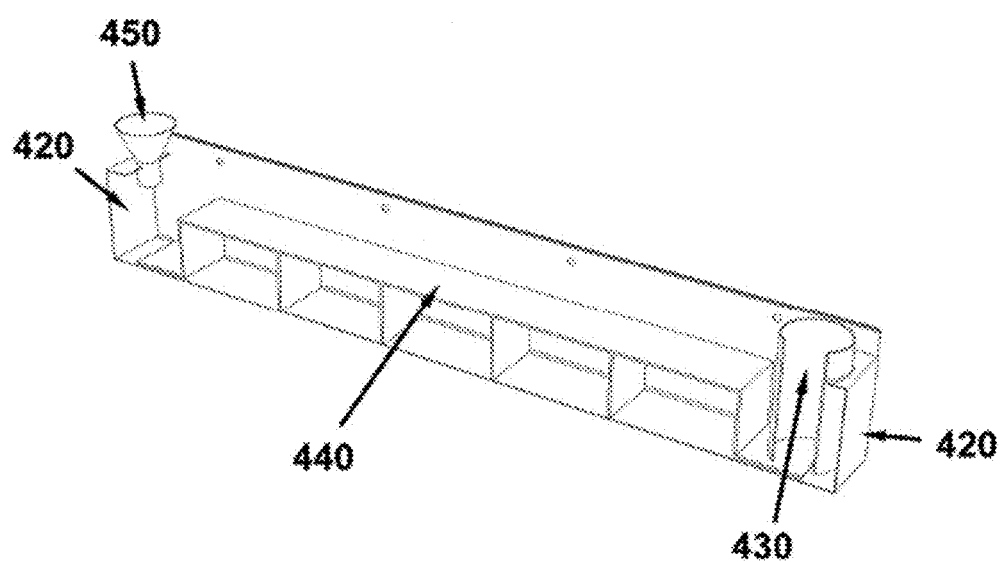
FIG. 4 shows a cross section of the device shown in FIG. 3.

Now referring to FIG. 4, the tank presented in FIG. 3 is shown in cross-section. The fill port 450 attaches to the left of two end walls 420 through a flange extension. Likewise, the float sensor housing 430 attaches by a flange extending from the right of the two end walls 420. Optional perforated metal baffles 440 serve to suppress splash surges of the liquid nitrogen when the assembly is in motion.

Figure 5:
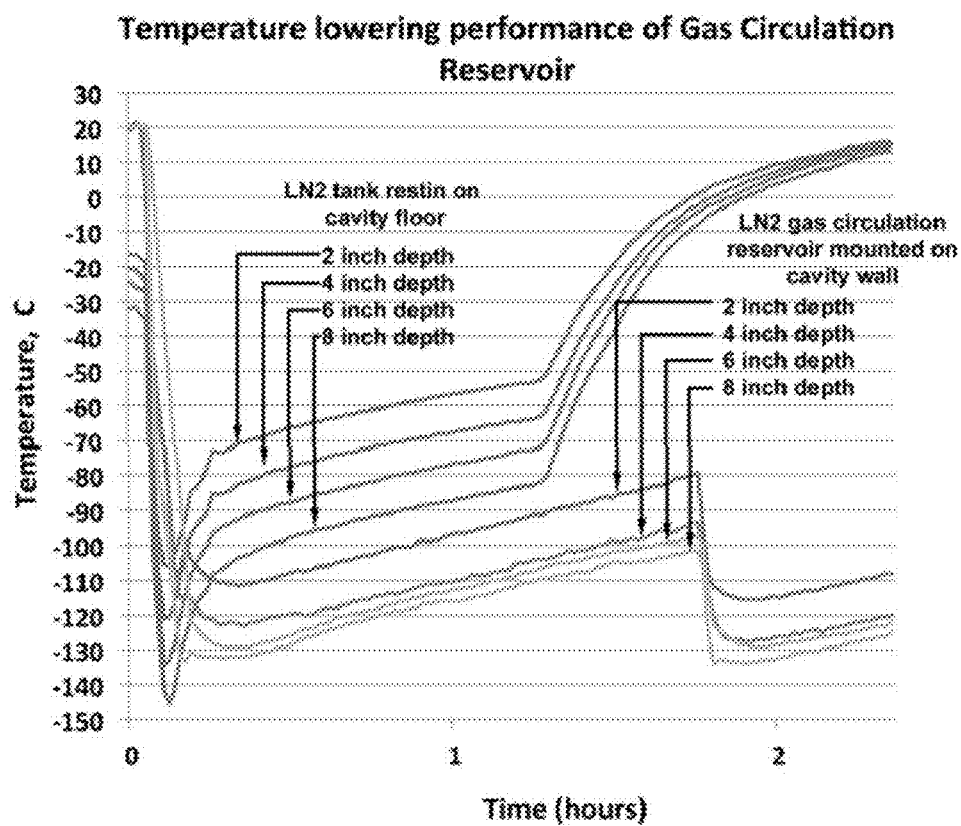
FIG. 5 shows a time graph of interior gas temperatures at various depths within the chamber of an embodiment of the device shown in FIGS. 1 and 2 under two operating conditions, one condition where liquid nitrogen is contained in a pan on the floor of the chamber, and another condition where the liquid nitrogen is contained in a gas circulation reservoir as shown in FIGS. 2, 3, and 4 was mounted on the chamber wall. The measurements of interior gas temperatures under the two sets of conditions demonstrate the effectiveness of the gas circulation reservoir in reducing the temperatures within the chamber while increasing the uniformity of the gas temperature.

Now referring to FIG. 5, the effect of the elevated gas circulation reservoir on the thermal performance of the invention is shown. In the figure, temperature measurements collected by thermocouple sensors fixed in a vertical array with a two-inch spacing are shown. Four traces are displayed from a test in which the liquid nitrogen was contained in a pan resting on the floor of a 26 inch long, 14 inch wide, and 9 inch deep chamber with the lowest of the sensors positioned 8 inches below the rim of the chamber. The traces show that the gas inside the chamber establishes a temperature gradient with the temperature at 2 inches below the rim being approximately 30 degrees Celsius warmer than the temperature 8 inches below the chamber rim. The temperature maintains a consistent rise over time for all sensors until the time at approximately 1.2 hours into the experiment at which the liquid nitrogen is exhausted. A second set of traces taken at the same positions were generated when a liquid nitrogen gas circulation reservoir, as shown in FIGS. 3 and 4, was mounted on the rear wall of the chamber and filled to a level that is one half of an inch below the front rim. The 4, 6, and 8-inch depth sensor traces are closely spaced indicating that the temperature in this region is more uniform and closer to the lower temperature range. In addition, the 2-inch depth temperature has been reduced by approximately 40 degrees Celsius while the 8-inch depth temperature has been reduced by approximately 25 degrees Celsius. The dimensions of the tanks used to produce the data were, for the first set of data with the tank resting on the chamber floor, 10 inches in length, 5 inches in width on a horizontal plane, and 2 inched in depth, and filled to a depth of 1.75 inches at the start of the experiment, while the tank mounted on the rear wall for the second set of data measured 26 inches in length, 2.75 inches in width on a horizontal plane, and 3 inches in depth. The tank was mounted onto the rear wall of the chamber such that the top edge of the front side of the tank was 1.4 inches from the rim of the container. The tank was filled to a depth of 2.5 inches at the start of the experiment.

Figure 6A:
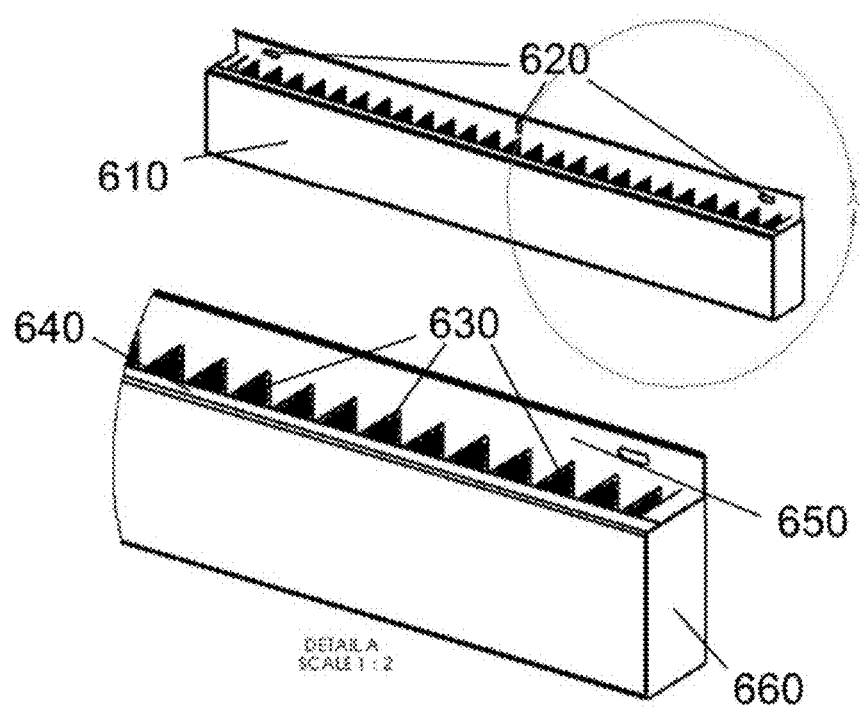
FIG. 6A shows a second embodiment of a liquid nitrogen boiler.

FIG. 6A illustrates another embodiment of a rectangular cross-section liquid nitrogen boiler. The boiler body is constructed from a rectangular U-shaped channel 610 that is enclosed by two seam-welded end plates 660 that form a liquid-tight tank. The tank is mounted by the back wall 650 to the rear inside surface of the cold chamber through the suspension slots 620. As the insulating material of the chamber case will have a different expansion coefficient than the metal material of the boiler, over the temperature range of room temperature to the lower range of the operating temperatures, the insulating material will need to contract and expand at a greater rate than will the boiler. For this reason, the mounting slots on the end are designed to be in a horizontal orientation to allow slippage on the mounting posts, while the central mounting slot is in a vertical orientation to maintain the central position of the tank. To suppress liquid sloshing during movement, the tank is equipped with a liquid return flange 640 on the front side, while the height of the rear wall 650 forms sea-wall to return liquid to the tank. To suppress liquid motion on the long axis of the tank, perforated metal baffles 630 are spaced at regular intervals of 1 inch. For applications in which more vigorous motion is anticipated, to suppress liquid motion, the baffle system can be replaced by porous materials such as, but not limited to, open cell urethane foam, ceramic foam, cellulose fiber, synthetic fibers, and metal mesh.

Figure 6B:
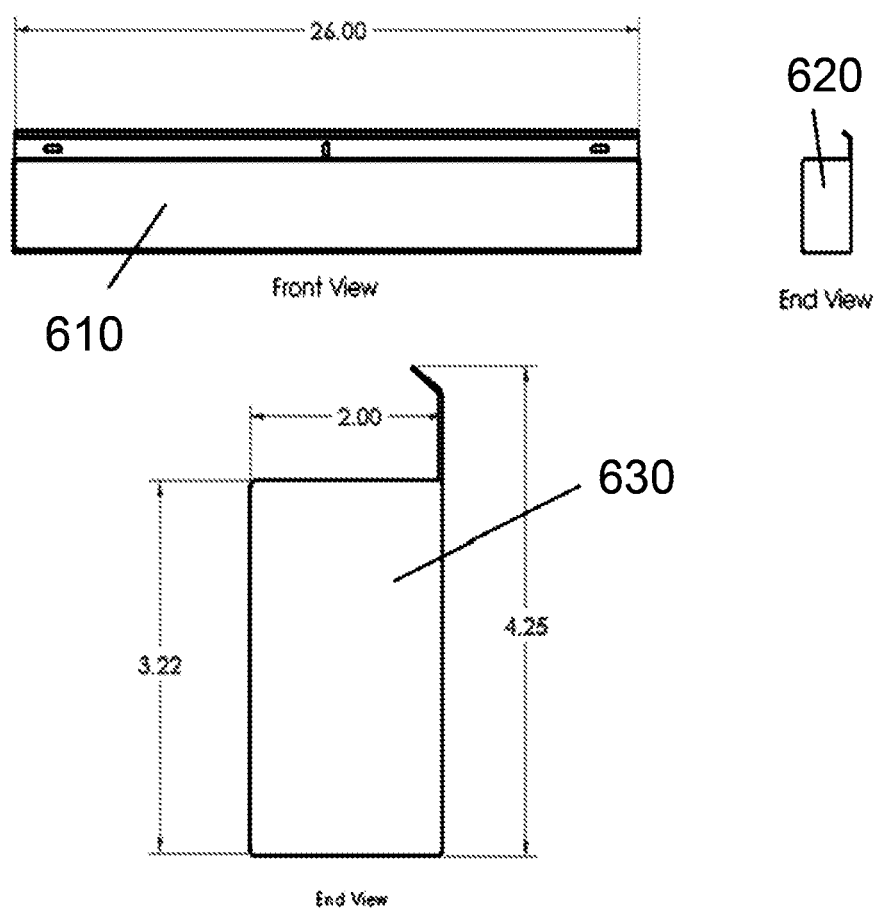
FIG. 6B shows exemplary dimensions of the device shown in FIG. 6A.

Now referring to FIG. 6B, the major dimensions of the boiler shown in FIG. 6A are shown. The boiler measures 26 inches in length with a front side height of 3.22 inches and a width of 2 inches. The height of the back wall of the boiler is 4.25 inches.

Figure 7:
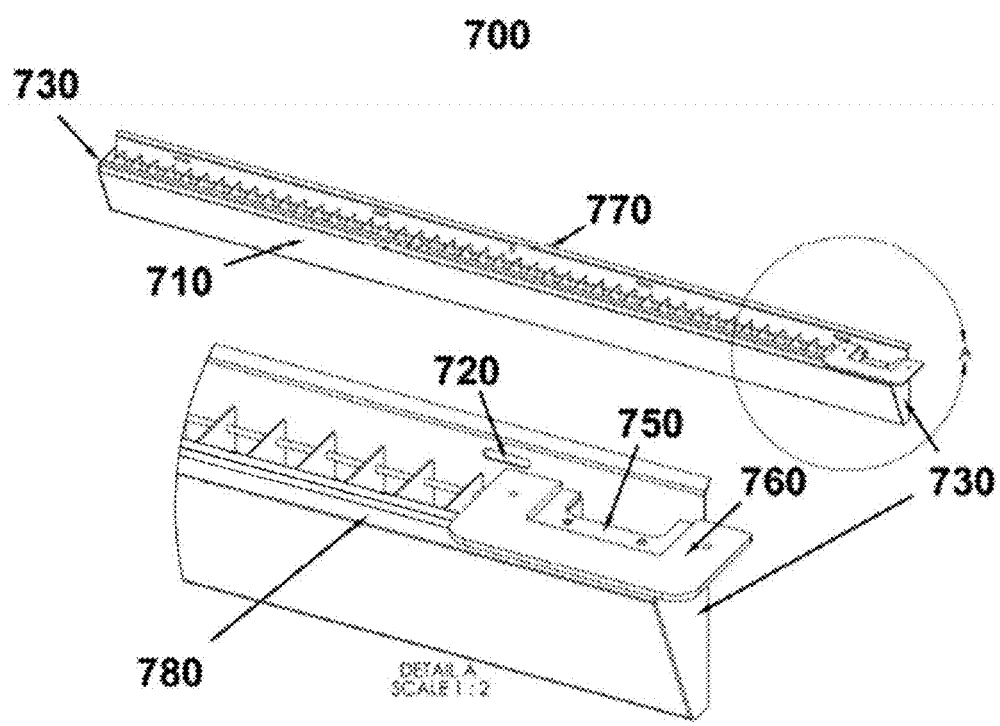
FIG. 7 shows a third embodiment of a liquid nitrogen boiler of the invention.

Referring to FIG. 7, an embodiment of the wedge cross-section liquid nitrogen boiler tank (the "V"-boiler) is shown. The boiler 700 comprises a single sheet of 20 gauge stainless steel bent to form a wedge cross-section channel that includes a back wall, underside, and front wall 710. To prevent splash ejection of the refrigerant during motion, a rearward projecting flange 780 is attached at the front upper edge. Seam welded to both ends of the wedge are end-caps 730 that form a liquid-tight trough. Multiple through-slots 720 are introduced into the back wall for the purpose of mounting the boiler on the inside wall of the working chamber of the cold gas container. An edge projection rearward from the back wall of the tank 770 adds rigidity to the back wall and forms a seal on the inside wall of the chamber to restrict gas and liquid flow behind the boiler. A sensor mounting plate 750 is welded to the right end of the tank and at the flange 780 interface, although in some embodiments, the sensor is mounted at alternate locations. In other embodiments, multiple sensors are installed on the same boiler. A sensor cover mounting plate 760 is attached to the sensor mounting plate. To suppress fluid motion, perforated metal baffle plates 780 are installed at regular intervals along the length of the tank interior. The cross-section profile of the boiler forms a V-shape.

The overall dimension of the V-boiler shown in FIG. 7 is shown in FIG. 8. The "V" refers to the shape of the reservoir cross section, while "boiler" refers to the boiling of the liquid nitrogen in the reservoir that provides the cold gas to the device. The boiler for the device shown in FIGS. 2-4 and 6A and 6B above, had a rectangular cross section and is useful in achieving chamber temperatures as low as −160 degrees C. The V-boiler is capable of regulating the temperature within the chamber to a range of −80 degrees C. to −50 degrees C. With the rectangular cross-section boiler, as the LN2 level decreased, the chamber temperature increased. The explanation for this observation is that the boiler exterior surface area opposite to the interior surface of the boiler that is in contact with the LN2 is a primary means of heat exchange with the gas on the exterior of the boiler. In addition, the lower the LN2 surface in the boiler and the smaller the surface area of the LN2 in the boiler, the lower the efficiency of direct heat exchange between the surface of the LN2 and the chamber gas. The cross section of the V-shaped boiler provides a more rapidly decreasing LN2 surface area as well as a more rapidly decreasing boiler surface area that is in contact with the LN2 as a function of the LN2 level within the tank than does a rectangular boiler wherein the undersurface is a constant value. The v-boiler increases the likelihood that a level can be found at which the chamber temperature is in a desired range. In other words, the V-boiler has a greater choking of the cooling capacity with LN2 level than does a rectangular boiler.

Once one correlates a desired liquid level in the reservoir that gives the correct temperature in the chamber, the present invention provides a number of ways to maintain that particular liquid level. In the test demonstration described below, the manual addition of LN2 at regular intervals was used to hold the chamber temperature in the desired range.

Figure 9:
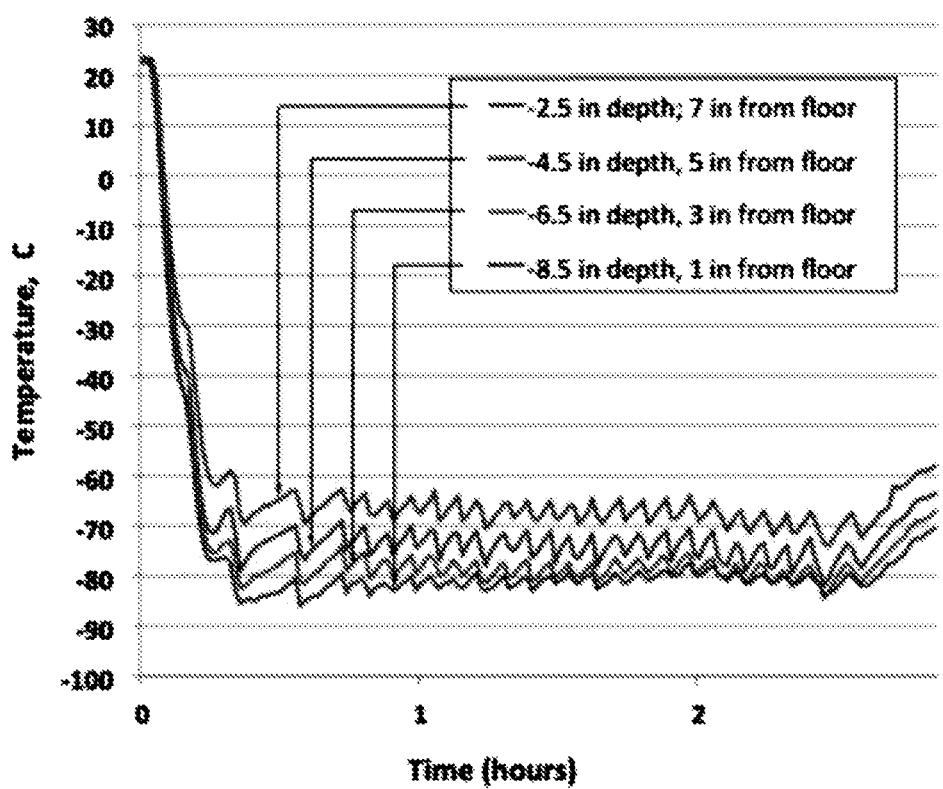
FIG. 9 shows a time graph of the interior gas temperatures at various depths within the chamber of an embodiment of the device container shown in FIGS. 1 and 2 operating on a liquid nitrogen boiler of the design shown in FIGS. 7 and 8. Using manual control of a liquid nitrogen delivery system and feedback from liquid nitrogen level observation and chamber gas temperature data, one can quickly establish a liquid nitrogen refill cycle that can maintain the chamber temperature within a 20 degree Celsius range of about −80 to −60 degrees Celsius.

Referring to FIG. 9, the results of a test that demonstrates that the V-boiler design is capable of holding an open gas chamber within a specified temperature range are shown. Periodic addition of LN2 to a boiler through the manual activation of a liquid nitrogen pumping system was performed to simulate a regulatory feedback loop. Based upon visual monitoring of the liquid nitrogen depth through the use of a rule scale in addition to temperature feedback from a four-thermocouple vertical array, liquid nitrogen was manually added by closing a switch that pumped LN2 into the boiler, then opening the switch when the correct level was reached. The thermocouple array provided the temperature at a height of 1 inch above the floor of a 9.5-inch deep chamber and at a height of 3, 5, and 7 inches above the floor. The chamber measured 16 inches in width and 27 inches in length. The boiler was 26 inches in length. In the test, the goal was to hold the temperature at the lowest thermocouple sensor at −80 degrees Celsius plus or minus two degrees. A refill cycle of approximately 45 seconds in duration every 5 minutes was discovered to hold the temperature within the specified range. The results show that using a feedback loop, a twenty degree temperature range could be established within a 6 inch deep test volume. The change in liquid nitrogen depth between the high and low phase of the fill cycle was 0.25 inches. Under the test conditions, the boiler consumed approximately 3 liters of liquid nitrogen per hour.

The results of FIG. 9 suggest that if a sensitive liquid nitrogen level sensor were to be applied, the result could be replicated by automating the filling process. For automatic filling of the LN2 reservoir, the invention provides a means for sensing the liquid level in the reservoir. In the test demonstration described in FIG. 9 the liquid level was regulated to a difference of a quarter of an inch, however, an even tighter control of the temperature cycle range can be achieved by further restricting the high and low LN2 level differential. With the very sensitive level detectors provided by the invention, tight control of the temperature in the chamber can be achieved.

Figure 12:
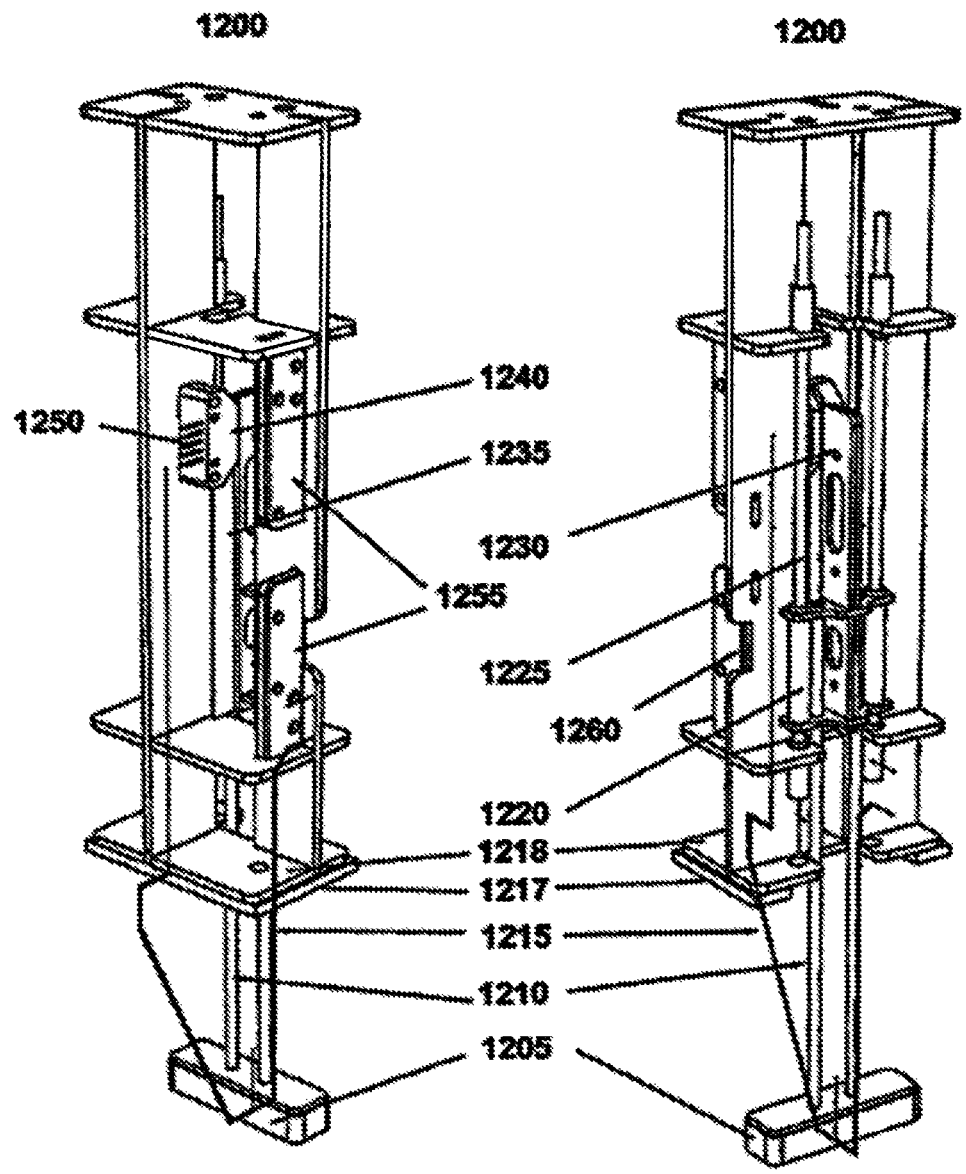
FIG. 12 shows an embodiment of a liquid level sensor of the invention for use with the liquid nitrogen boiler of the invention.

FIG. 12 shows one embodiment of a sensor 1200 designed to achieve the necessary level resolution for fine regulation of the chamber gas temperature in the invention. When attached to the V-boiler mounting plate (part 750 in FIG. 7; part 1217 in FIG. 12), by means of the sensor base 1218, the float 1205 is suspended in the boiler (cross section outline 1215 shown for placement reference) and will rise with the level of the liquid in the boiler, lifting the connection rods 1210 in the process. The connection rods 1210 will lift the sensor slide 1220 that is held to a vertical path by the two slide rods 1225. Attached to the side are two clamp plates 1230 which partially enclose a mylar code strip 1235 on which is a fine bar grid that provides a light-dark patter at a spacing of 200 cycles per inch. The grid code strip slides in a light sensor 1240 that will provide a high and low digital voltage signal through the connector pins 1250. The signal is carried by a ribbon wire bus (not shown) that is held by the clamp plates 1255 and exits through the bypass notch 1260 through the rear of the sensor housing (not shown). With a resolution of 200 cycles per inch, a quarter of an inch change in the float position will provide a count of 50 cycles, and can thereby provide enough sensitivity to monitor the LN2 level over the desired range. The level data can be used by a microprocessor to control the LN2 pumping system. Both the code strip and the sensor can be purchased commercially (from vendors such as US Digital; US Digital markets a suitable sensor, model EM-1).

Because the boiler is at a very cold temperature, and the sensor extends up into the room temperature gas, there is a thermal short circuit that will draw in environmental heat. If the sensor were made of a material with a high thermal conductivity, a large part of the sensor would be very cold and would condense atmospheric moisture as frost on the system, potentially interfering with the signal. Because the sensor comprises a sliding float level, any frost on this system could bind the sliding components. For this reason, the sensor is constructed from a material with a low thermal conductivity, such as carbon fiber sheet or epoxy fiberglass. The float shown is made from PE (polyethylene) foam Those of skill in the art will appreciate in view of this disclosure that the devices of the invention can be fully automated and equipped with a variety of sensors, alarms, and means for collecting, storing, and transmitting signals. Temperature sensors will often be employed with the device, and recordings made of the temperature measurements taken, which may be transmitted to other devices. Liquid level sensors may be employed for the reservoir. Alarms may be utilized and configured to alert the user to an undesired temperature change or the need to add coolant to the reservoir. In some embodiments, an attached or remote microprocessor receives signal input from a tank level sensor, from a temperature probe, or both a tank level sensor and a single or multiple temperature probes, and based upon the input signal received controls a refrigerant delivery system, and thereby controls the liquid level within the boiler tank. In some embodiments the microprocessor regulating the liquid refrigerant delivery is attached to a user touch screen interface. In some embodiments, the touch screen interface is physically attached to the cold gas container while in other embodiments the touch screen is remote from the cold gas container. In other embodiments, the microprocessor is linked to the device through a hardwired or wireless interface that sends sensor data back to the microprocessor and receives control signals from the microprocessor.

Figure 17:
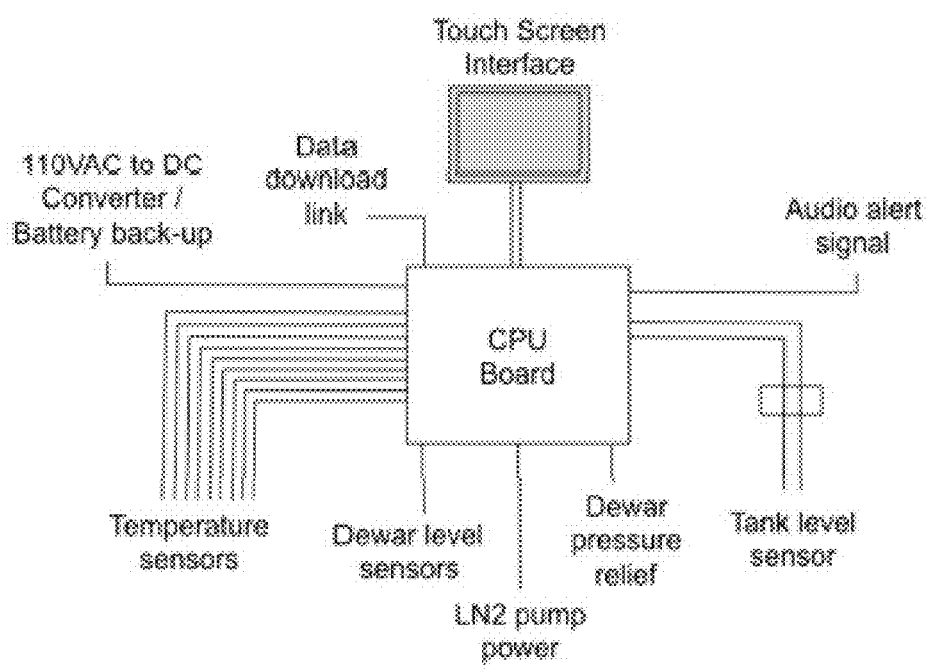
FIG. 17 shows an illustrative embodiment of signal linkages that can be received and sent from a device of the invention.

FIG. 17 shows an example of the signal linkages received and sent from an embodiment of the invention. In the schematic shown, the central microprocessor board receives input from eight separate temperature sensors in addition to signals sent from the refrigerant tank sensor(s), as well as liquid level sensors inside the refrigerant Dewar reservoir. The microprocessor board has output signal lines connected to the liquid nitrogen refrigerant pump or pressurization system and to a Dewar pressure relief valve that may be activated when the invention is in motion to prevent unintentional pressurization of the Dewar flask due to sloshing of the liquid contents onto the higher temperature walls of the container interior. The microprocessor board (the CPU Board) receives power from an higher voltage AC to lower voltage DC converter and is linked to a battery system for uninterrupted power when the invention is detached from the AC line. The microprocessor board has a port for data download through hardwire or wireless linkage and a touch screen interface, while in other embodiments, the visual interface is an LCD screen and the user input takes place through other methods including but not limited to mechanical switches or capacitive switches. An audio output signal is linked to a transducer to alert an operator to various conditions or states which the invention may be in.

Channels in the interior chamber wall may be included for the placement of thermometric sensor wiring. The channels run the entire interior wall perimeter at two levels that bracket the working depth of the cold gas, thereby providing feedback on the high and low range of the gas temperature. In some embodiments, the sensors may be mounted on sensor bars that are located at side positions near the boiler side of the work area and the front corners of the work area.

Figure 10:
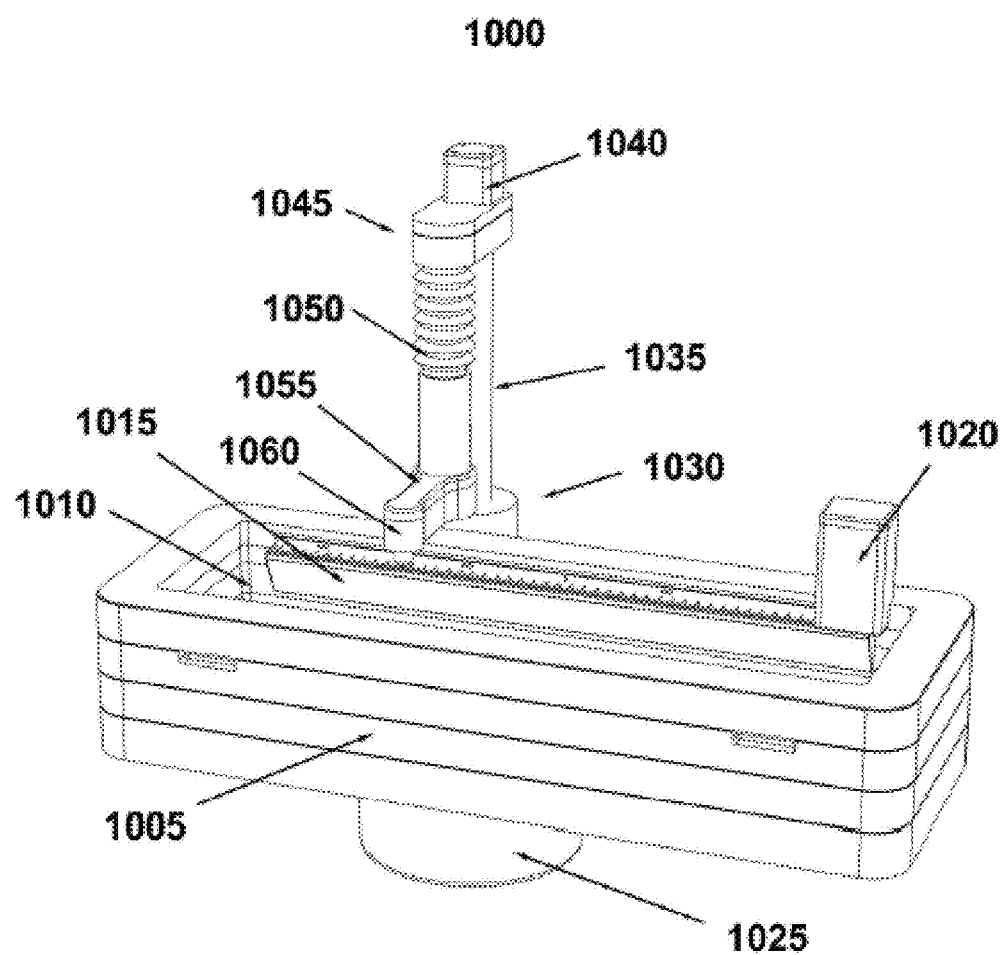
FIG. 10 shows an embodiment of a device of the invention suitable for simultaneous use by two individuals working side by side, as useful for a two-step process. The device holds the open chamber temperature to a specific range by active regulation of the liquid nitrogen level within the boiler tank. The figure shows the placement of a liquid level sensor for the nitrogen boiler and an embodiment of an atmospheric pressure liquid nitrogen delivery system that provides height adjustment capability for the gas chamber.

Now referring to FIG. 10, a level-sensor controlled embodiment of the invention is shown. In this embodiment 1000, a cold gas container 1005 with an interior chamber 1010 measuring 13 inches in width, 54 inches in length and 9.5 inches in depth is shown. Mounted on the V-boiler 1015 is a level sensor 1020. The sensor digital signal is fed to a microprocessor (not shown) that controls the pump system 1030 to deliver liquid nitrogen from a Dewar flask 1025 (partially shown; in place behind the container 1005). While an installation of the embodiment 1000 for use with robotic systems can be situated at a singular location and height, when the installation is configured for manual use, a dynamic working height option can be provided. Intermediate to large liquid nitrogen reservoirs are typically provided as pressure vessels that use the interior gas pressure as a delivery force to dispense the liquid through a hose or pipe. Flexible dispensation hose for cryogenic use is typically constructed with a corrugated inside diameter. As the liquid drops in pressure from the typical storage pressure of 20 PSI to atmospheric pressure, the boiling point of the liquid nitrogen is lowered. As a result, a portion of the liquid must expand to gas to lower the liquid temperature. As the evolving gas is released through the dispensation hose, a high decibel whistle is typically emitted from the hose. In addition, the nitrogen is dispensed as a mixture of gas and liquid, and a phase separation nozzle is frequently applied to suppress spraying and projection of the liquid. With a refresh cycle of 5 minutes for the boiler, were a pressurized liquid nitrogen system to be installed, a worker positioned at the station 1000 would experience the shrill sound of nitrogen gas release multiple times during a shift with a likely negative impact on the work experience. For this reason, the liquid nitrogen in the embodiment of the instant invention described in FIG. 10 is supplied from an atmospheric-pressure Dewar and delivered by an on-demand low-pressurization system consisting of a resistance coil that is submerged in the liquid nitrogen Dewar reservoir (not shown). In addition, while the liquid nitrogen expenditure to cool an un-insulated metal delivery hose may be acceptable for infrequent bulk delivery of the refrigerant, using the same hose for frequent intermittent liquid delivery would incur a significant accumulative refrigerant cost. For this reason, in the nitrogen delivery system shown in FIG. 10, the liquid nitrogen comes into contact only with synthetic materials with a low heat capacity and high insulation value, thereby greatly reducing the refrigerant cycle delivery cost as relatively little conversion of liquid nitrogen to gas occurs in transit from the cooling of the piping system. The system comprises an insulated riser tube 1035 that elevates the liquid to a phase separation dome 1040. The liquid then moves by gravity through the primary gravity chute 1045 and into a telescoping drop nozzle 1050, then to a secondary gravity chute 1055 to be subsequently dispensed through the fill nozzle 1060 into the boiler tank 1015. The secondary gravity chute system is held fixed in relation to the container 1005 and is mounted by a bracket to the container. As the container 1005 is raised and lowered, the telescoping drop nozzle adjusts in length to accommodate the change in distance between the primary and secondary gravity chutes.

Figure 11:
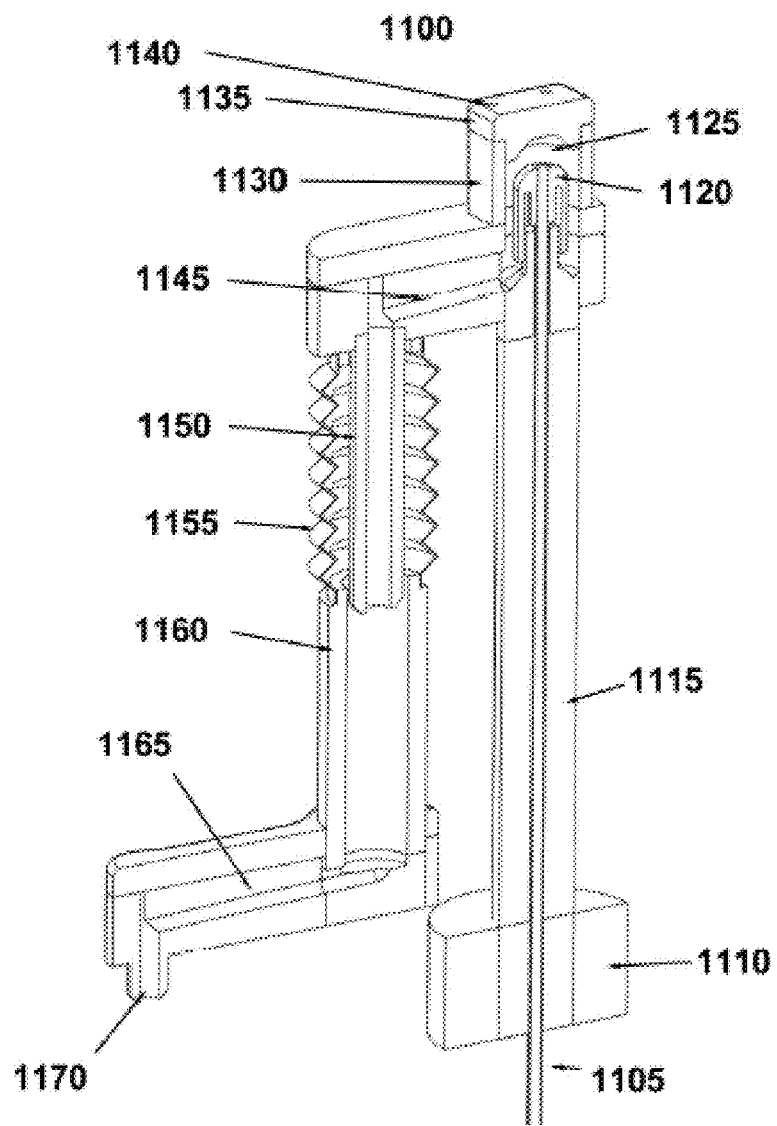
FIG. 11 shows a cross-section view of the liquid nitrogen delivery system shown in FIG. 10.

Now referring to FIG. 11, the liquid nitrogen delivery system described in FIG. 10 is shown in cross section detail. In this figure, the delivery system 1100 comprises an inner carbon fiber tube 1105 that extends through the pump system head 1110 into the phase separation dome chamber 1125. In some embodiments, upon the application of an electrical potential through the resistance coil in the Dewar, a pulse of nitrogen gas pressure on the order of 2 to 5 psi is generated within the Dewar thereby immediately lifting a column of nitrogen through the tube 1105. In other embodiments, the Dewar reservoir is pressurized at all times and the flow of liquid nitrogen is regulate by a electrically controlled valve. The liquid nitrogen and any evolving gas overflows the tube in the dome chamber 1125 within the dome 1130, and the liquid drains down the bubble head 1120 while the gas is released through the vent holes 1140 in the dome lid 1135. The liquid nitrogen flows downward into the primary gravity chute 1145 to the telescoping drop nozzle 1150 that is surrounded by the flexible bellows 1155, and drains into the cylindrical funnel 1160. The nitrogen liquid flows into the secondary gravity chute 1165 and exits through the dispensation nozzle 1170 into the liquid nitrogen tank.

While the gas pressure is used in the instant invention to deliver the liquid nitrogen from the Dewar flask, in other embodiments, the liquid nitrogen is lifted through the tube 1115 by means of an electric impeller pump.

Figure 18:
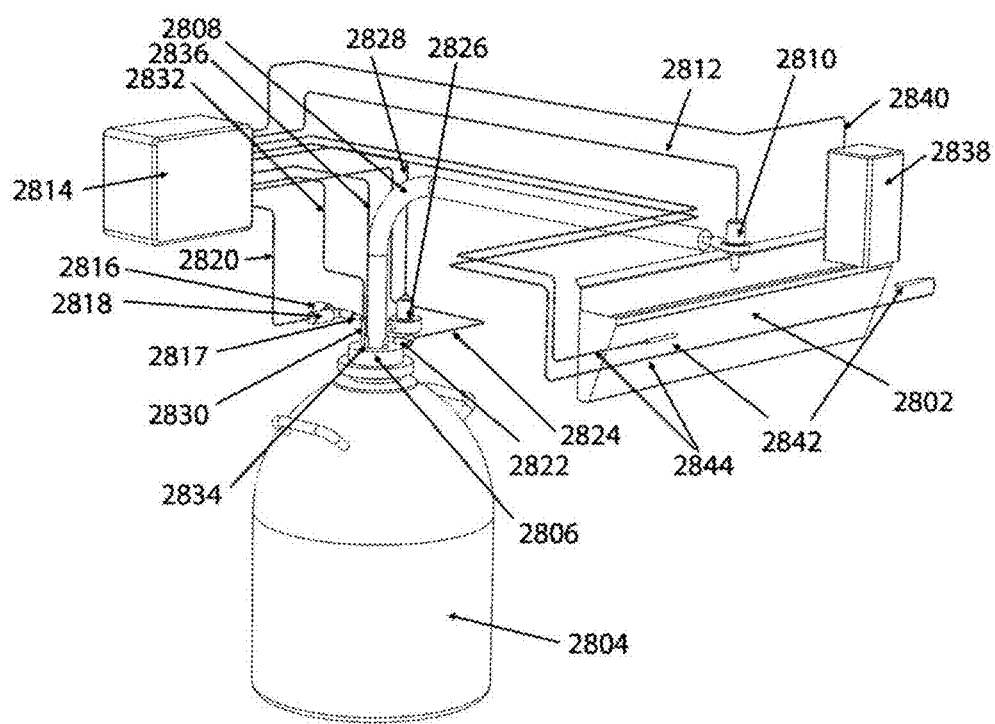
FIG. 18 shows an embodiment of a liquid nitrogen delivery and flow regulation system.

FIG. 18 shows an embodiment of a liquid nitrogen delivery and flow regulation system that may be used to regulate the temperature of a cold cavity. In this embodiment, liquid nitrogen is delivered to the liquid nitrogen boiler 2802 from the storage Dewar flask 2804. The liquid nitrogen flow pathway comprises an internal siphon tube and line filter (not shown) that passes through the Dewar flask manifold 2806 and into the insulated delivery conduit 2808. The conduit terminates in an electrically controlled valve and spigot 2810 that is operated by an electrical signal through the control lead 2812 that carries an output signal from a central processing control board (not shown) that is contained within the instrument housing 2814. The liquid nitrogen storage Dewar 2804 is filled through a coupling connector 2816 attached to a feed-line 2817 that enters into the manifold 2806. The liquid nitrogen inflow to the Dewar is regulated by an electrically controlled valve 2818 that receives signals from the control board on the control line 2820. During the Dewar filling cycle, internal back-pressure in the Dewar is released by the electrically controlled gas release valve 2822 that is operated by signal control line 2824. The central processing board receives the Dewar pressure data signal from the pressure transducer 2826 through the data signal line 2828. The Dewar liquid level sensor 2830 provides a data input signal to the processor board through signal line 2832. The Dewar can be pressurized by activation of an electric resistance coil 2834 that is submerged in the liquid nitrogen. Upon the application of an electric current through power line 2836, the evolved heat of the coil will vaporize some of the liquid nitrogen thereby raising the internal pressure of the Dewar flask. One or more liquid nitrogen level sensors 2838 are used to monitor the fluid level in the boiler 2802 and the level data signal is received at the processor board as a signal on line 2840. The temperature of the cold cavity (not shown) that is cooled by the liquid nitrogen boiler 2802 is sensed by one or more sensors 2842 and the temperature data input signal is transmitted to the processor board over signal leads 2844. Through computational analysis of the feedback data from the level sensors 2838 and the temperature sensors 2842 the central processing board will regulate the amount of liquid entering into the boiler 2802 thereby controlling the level of the liquid nitrogen and therefore controlling the temperature of the cool cavity.

Figure 13:
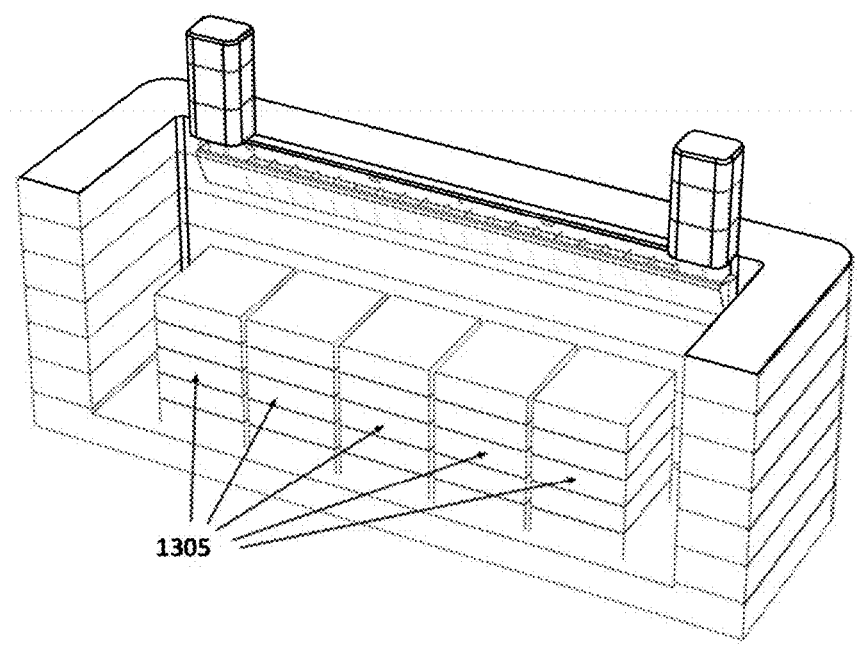
FIG. 13 shows a cross-section view of an embodiment of the invention that is designed to contain and cool stacks of tray containers.

FIG. 13 shows a device (the "tray chilling module") configured to hold tray stacks 1305 that are to be filled with vials. Stacks of five trays are indicated. It will be appreciated that a number of configurations are possible. For example, the device can be configured hold a standard freezer rack containing ten storage boxes. The container can be varied to accommodate any rack height (the rack is positioned on its side in this "shuttle module").

Figure 14A:
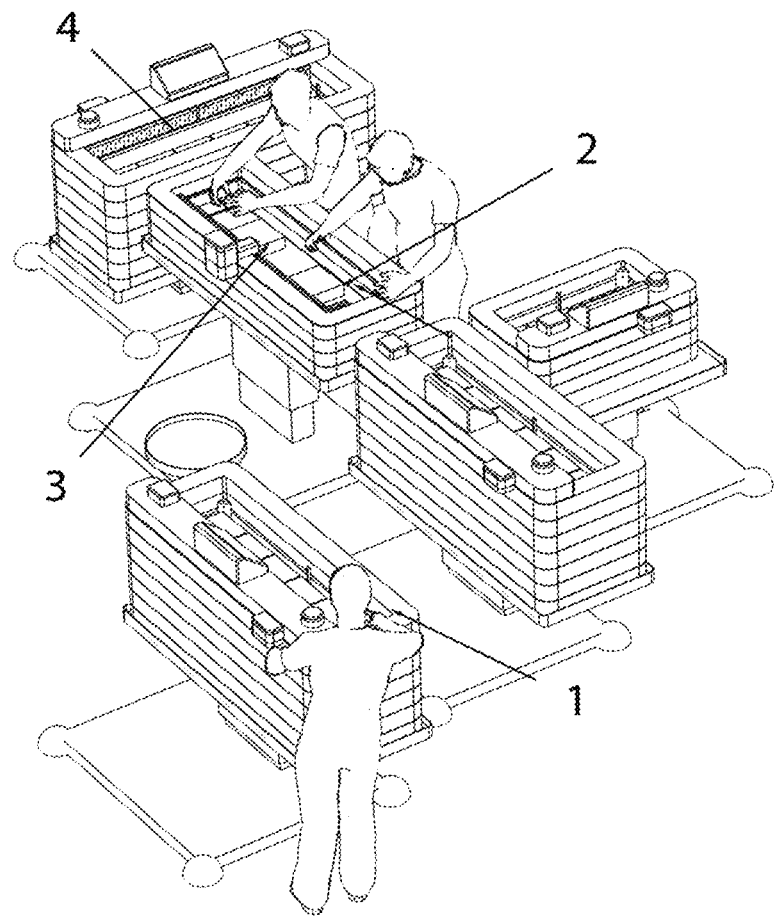
FIG. 14A shows a process flow layout for using a cryogenic device.

FIG. 14A illustrates how a series of the devices can be used together to perform complex operations. In FIG. 14A three individuals work to transfer vials into cartons and sealing the cartons. At station (1), carton trays are prechilled and container is moved to the transfer position. At station (2), cryobox and carton trays are moved to transfer container. At station (3) cartons are loaded with vials and passed to carton closing station. At station (4), loaded cartons are closed, then trays are laced into the buffer station. When full, trays are moved to freezer.

Figure 14B:
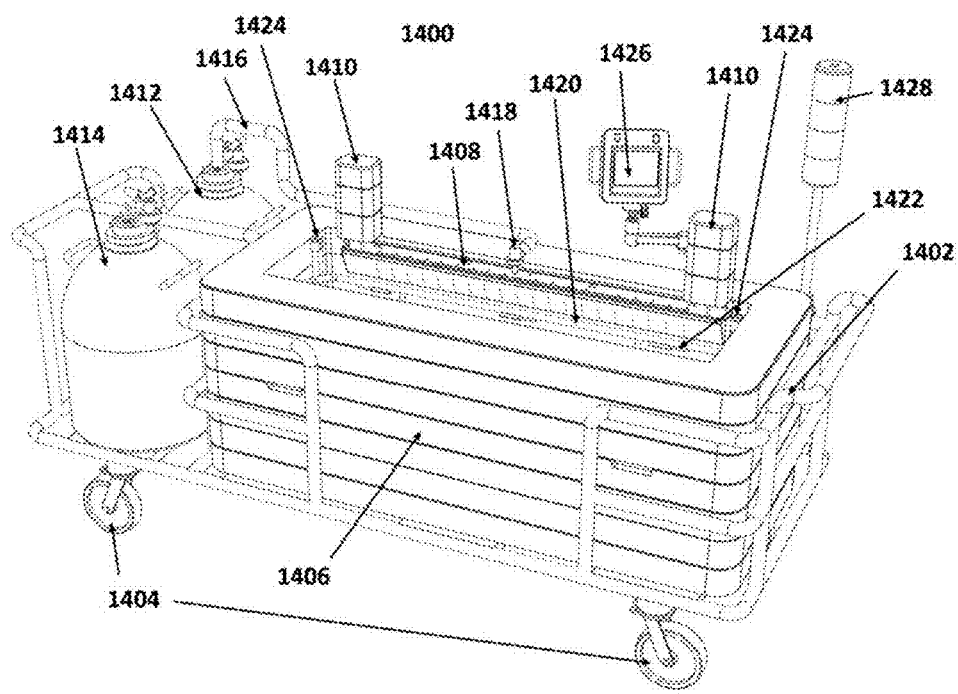
FIG. 14B shows a device used in combination with a specially equipped cart.

FIG. 14B illustrates the mobility of the devices. As the figure illustrates, the devices of the invention can be placed on wheeled carts to make them mobile, and the invention provides a number of specially adapted carts. Carts of the invention may include one or more of the following: (i) a storage tank for coolant; (ii) a pump or pressure system for transferring coolant from the coolant reservoir to the boiler tank of the device; (iii) a power supply; (iv) a battery charger; (v) a voltage converter; (iv) means for raising and lowering one or more cart surfaces, (v) handles for manual propulsion of the cart, (vi) impact guards for sensitive equipment, and (vii) liquid nitrogen piping, phase-separators, gravity chutes, and mounting features for the same. In FIG. 14B, a stainless steel tubular frame cart 1402 is mobilized on a set of four caster wheels 1404 and supports an insulated chamber 1406. The chamber is refrigerated by a liquid nitrogen boiler 1408 comprising dual liquid level float sensors 1410. The boiler is supplied with liquid nitrogen stored in the primary 1412 and secondary 1414 Dewars through an insulated pressurized feed line 1416 that terminates at an electrically-controlled valve 1418. The main microprocessor board (not shown) receives and processes the boiler liquid nitrogen level data from the level sensors 1410, and chamber temperature data from a series of temperature sensors 1422 attached to a tubular harness 1420 to regulate the liquid nitrogen delivery through the control valve 1418. The temperature sensor lead wires (not shown) exit the sensor harness 1420 through ports 1424 to connect with the central processing board. The operational status of the embodiment 1400 is displayed on the videographic display monitor 1426. Fault conditions in the operation of the embodiment 1400 are visually announced by a colored light tower 1428.

Those of skill in the art will appreciate in view of this disclosure that the devices of the invention can be fully automated and equipped with a variety of sensors, alarms, and means for collecting, storing, and transmitting signals. Temperature sensors will often be employed with the device, and recordings made of the temperature measurements taken, which may be transmitted to other devices. Liquid level sensors may be employed for the reservoir. Alarms may be utilized and configured to alert the user to an undesired temperature change or the need to add coolant to the reservoir.

As the cooling power of the liquid nitrogen boiler can be augmented by increasing the surface area and refrigerant volume, the cooling capability is scalable. In addition, the cold gas within the chamber, being at higher density, will flow to fill the extents of the chamber displacing warmer and less dense gas. Providing liquid nitrogen boilers placed at appropriate intervals to hold the desired gas temperature range, one can construct a working chamber of any length in accordance with the invention. Bends can be introduced into the long container to accommodate floor layout plans, production flow requirements, and process sequence optimization.

A complete loop of trough-shaped containers can be constructed in an unlimited variety of layouts and sizes in accordance with the invention. For example, for robotic arm activity, a circular trough may be an optimal configuration so as to take advantage of a central robotic pivot point.

In some embodiments, multiple containers may be constructed in with one or more side-walls modified such that two or more containers can be joined to form longer or more complex modular assemblies allowing a continuous well or trough of low temperature gas. Such arrangements can allow the construction of extended or complex working systems in which operations may be conducted without the need to expose materials contained therein to external environments or temperatures. In some embodiments, the containers may be joined, for example and without limitation, an internal or external flange joint, an adhesive joint, a magnetic joint, a fusion weld, a clamp, or an integral permanent or reversibly attachable interlocking feature. In some embodiments, the multiple section container structures form a linear structure, while in other embodiments the containers form complex pathways, for example and without limitation, to allow enhanced access or strategic placement of personnel, machinery, or robotic systems. In some embodiments, the joined containers form a self-intersecting assembly allowing, for example and without limitation, a robotic arm to circumnavigate the container from a central location without removing portions of the arm from the cold gas interior. In other embodiments, the self-intersecting trough is formed from a single piece of material such as, for example and without limitation, a molded or machined foam trough. In some embodiments, one or more of the joining containers of an extended system may be covered. In other embodiments, one or more joined containers may not comprise a coolant tank, for example and without limitation, to act as adapters, extenders, joints, elbows, or bends in a continuous chamber system.

FIGS. 15A-D illustrate trough embodiments. In some embodiments the chamber can be described as a linear trough (FIG. 15A), a serpentine trough (FIG. 15B), or a zigzag trough. In some embodiments the trough may be branched. In some embodiments a branched trough has a single intersection (e.g., a "Y-shaped" or "T-shaped" trough). In some embodiments the trough forms a closed or continuous loop.

Figure 15A:
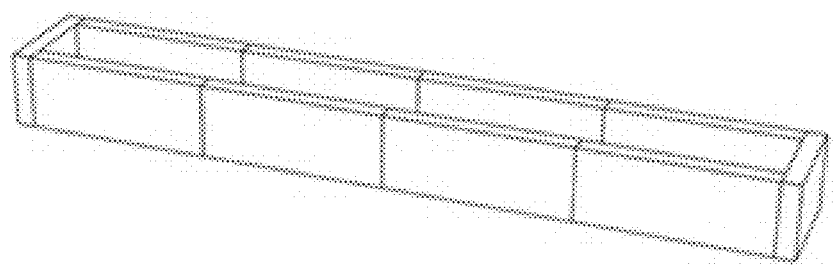
FIGS. 15A, 15B, 15C, and 15D illustrate trough configurations useful for production processes that require multiple steps while maintaining the production steps in an ultra-cold environment. (A) A linear trough configuration; (B) A serpentine trough configuration; (C) A closed loop configuration, illustrating that a container housing may be produced in modular format and assembled; (D) A "partially covered" embodiment.
Figure 15B:
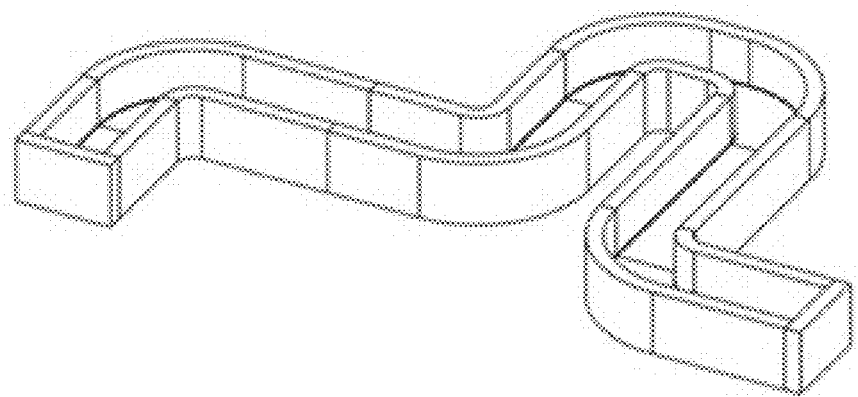

FIG. 15B illustrates that bends can be introduced into the long container to accommodate floor layout plans, production flow requirements, and process sequence optimization. A complete loop of trough-shaped containers can be constructed in an unlimited variety of layouts and sizes in accordance with the invention. For example, for robotic arm activity, a circular (ring shaped) trough may be an optimal configuration so as to take advantage of a central robotic pivot point.

Figure 15C:
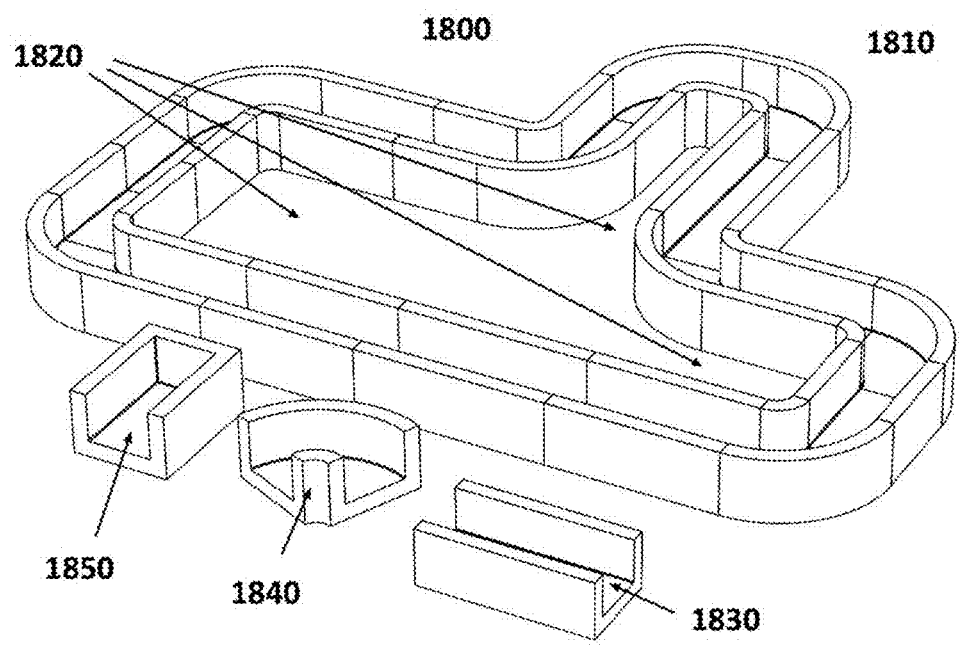

FIG. 15C shows an illustrative layout 1800 of a trough container raceway 1810. The trough system comprises three U-loops 1820 of various sizes in which personnel or robotic elements may be stationed. The construction of the trough raceway is modular, comprising straight modules 1830 and elbow modules 1840. The trough terminal module 1850 shown would be used as end-pieces in an open loop configuration. In some embodiments the trough forms an annular loop. In some embodiments, the loop comprises four linear segments, having the path defined by two concentric squares. In some embodiments, multiple containers or container parts may be constructed in with one or more sidewalls modified such that two or more containers or parts can be joined to form longer or more complex modular assemblies allowing a continuous well or trough of low temperature gas. As used herein, "modular" has its normal meaning of employing or involving a module or modules as the basis of design or construction. In the context of the invention, the container is constructed from a selection of preformed modules that can be combined in a variety of ways to provide containers with a variety of structure and chamber paths and path lengths. Such arrangements can allow the construction of extended or complex working systems in which operations may be conducted without the need to expose materials contained therein to external environments or temperatures. In some embodiments, the containers may be joined, for example and without limitation, an internal or external flange joint, an adhesive joint, a magnetic joint, a fusion weld, a clamp, or an integral permanent or reversibly attachable interlocking feature. In some embodiments, the multiple section container structures form a linear structure, while in other embodiments the containers form complex pathways, for example and without limitation, to allow enhanced access or strategic placement of personnel, machinery, or robotic systems. In some embodiments, the joined containers form a self-intersecting assembly allowing, for example and without limitation, a robotic arm to circumnavigate the container from a central location without removing portions of the arm from the cold gas interior. In other embodiments, the self-intersecting trough is formed from a single piece of material such as, for example and without limitation, a molded or machined foam trough. In some embodiments, one or more of the joining containers of an extended system may be covered. In other embodiments, one or more joined containers may not comprise a coolant tank, for example and without limitation, to act as adapters, extenders, joints, elbows, or bends in a continuous chamber system.

In some embodiments the chamber has a trough configuration with a chamber path length that is more than five times, more than six times, or more than 8 times the width of the chamber. In some embodiments the chamber has a trough configuration with a chamber path length of more than 3 feet, more than 6 feet or more than 10 feet. In some embodiments, the chamber length is 3 to 30 feet, such as 5 to 20 feet, such as 8 to 12 feet.

Figure 15D:
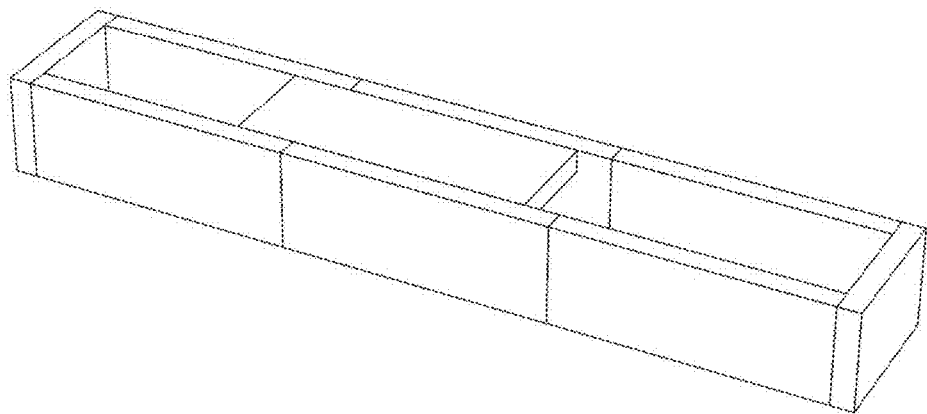

In some embodiments, some portions of the chamber are covered and other portions are open (FIG. 15D).

As used herein, "chamber path length" refers to the distance through which an object can be transported in the chamber (i.e., from one end to the other, or, in the case of a closed loop, from a starting position back to the same position). For illustration, rectangular chamber with an overall length dimension of 4 feet also has a 4 foot chamber path length. In contrast, a serpentine or ring-shaped chamber with a 4 foot overall dimension will have a longer path length. For example the path length of 4-foot diameter a ring-shaped (annular) chamber is about 12.5 feet (the circumference of the larger of the two concentric circles defined by walls of the chamber).

Figure 16:
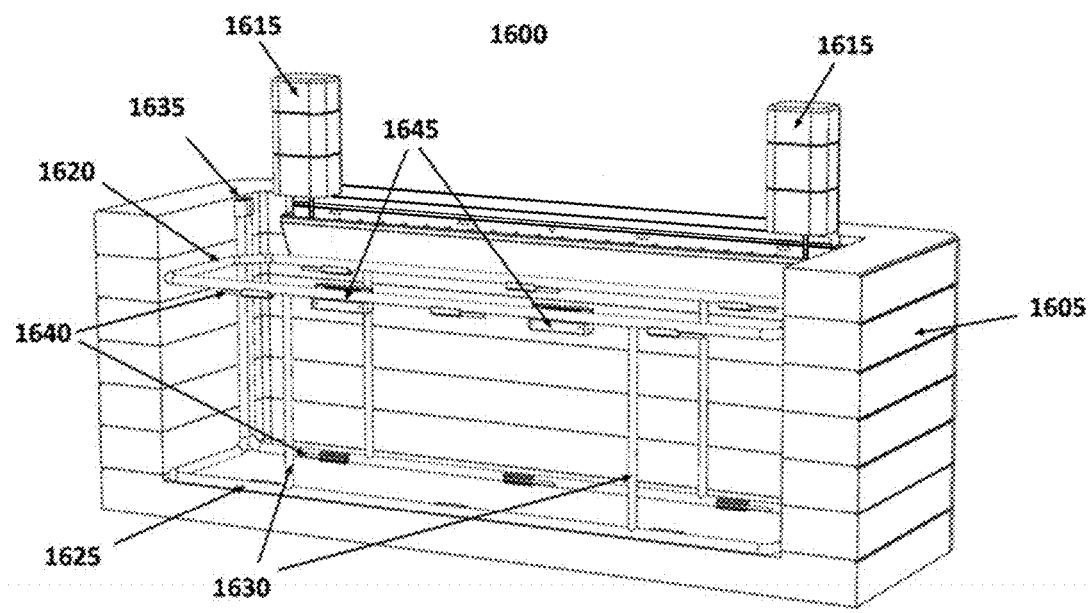
FIG. 16 shows a cross-section view of an embodiment of the invention comprising a liquid nitrogen cooling system and a temperature sensor and laser boundary indicator harness.

In some embodiments, the chamber temperature is monitored by one or more temperature sensors. In other embodiments the temperature sensors are removably held in position by a sensor harness that also routes and protects the sensor lead wires. In some embodiments, the sensor harness supports an array of sensors in one or more horizontal planes so that the temperature at all regions of the a given plane in the chamber interior may be monitored. In some embodiments the upper and lower planes that bound a designated working region may be monitored by a horizontal array of sensors. In an some embodiments, the sensor harness is selectively mounted to the chamber wall, while in other embodiments the harness is an independent and self-supporting structure. As shown in FIG. 16, a self supporting sensor array structure may be comprised of an upper sensor array 1620 and a lower sensor array 1625 that are connected by vertical support members 1630. Temperature probes 1640 may comprise any type and/or number of temperature probe known in the art. In one embodiment, temperature probe 1640 comprises a resistance temperature detector (RTD) sensor. In another embodiment, temperature probe 1640 comprises a thermocouple sensor. Temperature probes 1640 may further comprise any size and length, as may be desired. For example, in one embodiment a temperature probe is provided having a length of approximately 4.5 inches, and a diameter of 0.25 inches.

The sensor harness 1620 of the invention may generally comprise any size, shape and/or configuration that is compatible with the intended purposes disclosed herein. In some embodiments, sensor harness 1620 comprises a rigid, temperature resistant material, such as aluminum, stainless steel, or carbon fiber tubing. In some embodiments, the sensor harness is constructed from a solid tubing into which access ports are introduced while in other embodiments the sensor harness comprises sensor lead wire conduits constructed from interlocking channels.

Sensor harness 1620 of the embodiment shown in FIG. 16 comprises a tubular, conduit material having a hollow interior through which the temperature probe lead wires and other circuitry may be routed and/or stored. In some instances, the temperature probe lead wires are routed to an outlet adapter 1635 through which the wires (not shown)

exit rack 1620 and container system 1600. The exposed portions of the lead wires may further be routed through a flexible nylon conduit (not shown) and the ends of the lead wires may be operatively coupled to a display unit, temperature meter, and/or other temperature sensing equipment, as discussed above. In some embodiments the harness 1620, 1625 comprises a grounding wire that connects the harness structure to the earth ground potential.

Sensor harness 1620 generally comprises a shape that approximates the inner dimensions of chamber 1605 such that rack 1620 occupies the inner perimeter of chamber 1605. As thus configured, rack 1605 may be positioned within the interior of chamber 1605 with minimal effect on the available working space area of the container system.

In some instances the upper and lower horizontal boundary planes of the working space are monitored by a horizontal array of temperature sensors while is other embodiments, only the upper, the lower, or a selected plane between the upper and lower boundary planes will be monitored by an array of temperature sensors. In some instances, a sensor harness 1620 is positioned by means of supporting structures that are in contact with the chamber floor, while in other embodiments the sensor harness 1620 is suspended above the chamber floor by a plurality of hangers that directly engage supports embedded into the inner walls of the chamber (not shown In some embodiments the embedded supports comprise a plurality of hanger engagement structures such that the height of the sensor harness is adjustable.

With continued reference to FIG. 16, sensor harness 1620, 1625 may further comprise one or more temperature sensor adapters having a first aperture for receiving rack 1620, 1625, and a second aperture for receiving a temperature probe 1640. The sensor adapter may comprise any length or dimension desired. In some instances, a pathway is provided between the first aperture and the second aperture, whereby the temperature probe lead wired may pass from the second aperture and into the hollow interior of rack 1620, 1625 via the first aperture. Thus, the temperature probe lead wire is completely concealed within sensor adapter and rack 1620, 1625.

The sensor adapter generally comprises a non-thermoconductive material, such as a cross-linked polyethylene foam, a urethane foam, a styrene foam, a polyvinyl foam, or a polymer blend foam. As such, temperature probe 1640 is thermodynamically isolated from rack 1620, 1625, and may therefore accurately monitor the temperature of the working space without interference from the sensor rack material. In some instances, the position of sensor adapter is fixed via at least one of an interference fit or an adhesive. In other instances, the position of sensor adapter on rack 1620, 1625 may be adjusted by the user, as desired.

Sensor harness 1620 may further comprise one or more spread-beam lasers 1645 that is coupled to rack 1620. In some instances, leveling lasers 1645 comprise power lead wires that are routed through the hollow interior of rack 1620, and which exit rack 1620 via outlet adapter 1635.

A detectable indicator of the boundary or upper limit of the low temperature zone is useful in the practice of the invention to ensure that sample is not moved out of the low temperature zone into upper regions of the container that may be outside the desired temperature range. A variety of methods may be used for such delineation including coloration (e.g., an indicator line printed on a chamber wall) or lights (e.g., embedded LED lights) positioned on the chamber wall at a specified height corresponding to the top of the low temperature. In one approach, the system may be equipped with spread-beam or line lasers, for example as shown FIG. 25, which project a linear guideline which indicates an upper, or maximum level of a controlled temperature working environment. Generally, the laser is suitable for projecting light along a horizontal path across the chamber at the level of the upper boundary of the low temperature zone.

In certain embodiments a "line laser" is used to delineate the upper boundary of the low temperature zone. Line lasers (sometimes referred to as "fan lasers") project a horizontal laser line ("laser leveling line" or "fan array"). In some embodiments a horizontal rotary laser is used. Lasers are commercially available from a variety of sources including Quarton Inc., 17700 Castleton St., City of Industry, Calif. 91748 (1 mW 650 NM line laser part number VLM-650-27-LPA) and Johnson Level, 6333 W. Donges Bay Road-|Mequon, Wis. 53092). In some embodiments a "self-leveling" laser is used.

Referring to FIG. 16, laser 1645 may further be provided to project a linear guideline which indicates an upper, or maximum level of a controlled temperature working environment. In some instances, lasers 1645 comprise a laser line filter that is configured to project a laser leveling line at one or more surfaces of container 1605. In one embodiment, a first laser 1645 projects a laser line in an x-axis, and a second laser 2122 projects a laser line in a y-axis. Lasers 1645 may further comprise adjustable mirrors to facilitate fine tuning of the laser leveling lines.

In one aspect the cryogenic system is characterized by a chamber containing a combination of at least one temperature sensor and at least one detectable indicator (e.g., laser projection of a linear guideline). In one aspect the cryogenic system is characterized by a chamber containing the combination of a temperature sensor and detectable indicator (e.g., a laser line projection) where the sensor and indicator are positioned at the same or essentially the same height above the chamber floor. As used herein, "essentially the same height" means the sensor and indicator are at the same height plus or minus 1 inch, or plus or minus 0.5 inches. The laser is suitable for projecting light along a horizontal path at the same level as (in the same plane as) the sensor. Preferably the laser light traverses the interior of the chamber such that an object in the chamber that extends into or is transported through the horizontal plane at the level of the sensor is illuminated by laser light.

In one embodiment, laser 1645 comprises a single housing in which is housed two or more lasers. The laser housing is generally compact and comprises a minimum profile to prevent interference with the work area of the chamber. In some instances, the laser housing has a length of approximately 5 inches, a depth of approximately 1.5 inches, and a height of approximately 1.4 inches. In another embodiment, the two or more lasers are housed within the housing at an outward angle of approximately 30° from a central axis of the housing. See FIGS. 19 and 23.

In one embodiment, the present invention provides a device that enables a user to handle, manipulate, transfer, and package materials in an ultra-low temperature environment without the user being wholly exposed to those low temperatures. The devices of the present invention have a wide variety of applications. For example, the environmentally controlled packaging systems of the present invention may be used for various processes, such as work-in-progress labeling of vials being transferred from freezers to a packaging line; transferring pre-conditioned packaging components (cartons and packaging inserts) from freezers to a packaging line; transferring finished drug product from a packing line to a freezer; and transferring labeled drug product vials into final product container within a −80° C. to −50° C. working environment of a packaging station.

Below are provided various non-limiting examples which illustrate the utility of some of the devices and embodiments of the present invention. In particular, the following examples illustrate various systems, methods and devices that provide an ultra-low temperature solution for packaging temperature-sensitive products and materials. Some embodiments of the instant invention ensure a working range of −80° C. to −50° C. which protects the integrity of the product, packaging, and personnel involved in the packaging process. Other embodiments comprise a plurality of individual modules that are combined together to provide an ultra-low temperature environment, wherein the combined modules comprise a complete product packaging operation which ensures user safety and comfort, as well as maximizes ease of product throughput and scalability. Further, in some embodiments a multiple-module packaging station is provided having one or more mobile modules, and one or more stationary modules, wherein the mobile and stationary modules comprise a complete product packaging operation. Those skilled in the art will recognize in view of this disclosure that any possible configuration or mobile and/or stationary devices can be deployed as needed, or desired, in accordance with the invention.

Some embodiments of the present invention further comprise a harness (or harnesses) as a means for supporting and suspending one or more components within the chamber at a desired height above the floor of the chamber. The harness may have a length approximately equal to the inner perimeter of the container's chamber, whereby the harness is positioned within the chamber and circumscribes the inner perimeter. In one embodiment the harness is rectangular with dimensions of about 47 inches by about 12.5 inches.

Components that may be supported by or attached to the harness include temperature sensors and lasers, as described below. Thus harnesses may be referred to as a "sensor harness", a "laser harness", a "sensor and laser harness" and the like. It will be appreciated that, as apparent from context, one or more lasers may be attached to a "sensor harness", one or more sensors may be attached to a "laser harness", etc.

The harness may comprise a hollow tube having terminal ends in which are provided openings through which the hollow interior of harness may be accessed. In at least one embodiment, harness comprises a metallic material, such as stainless steel. A hollow interior of a harness provides a lumen through which lead wires may be ran to provide power to the various components supported on harness. Generally, the lead wires are fed through the openings in terminal ends.

In some instances, harness comprises a plurality of slot openings on a bottom or under surface of harness. Openings are configured to receive one or more temperature sensors, as discussed above. By placing openings on under surface, the temperature sensors are directed downwardly into the chamber, thereby optimizing their position for sensing the temperature within the chamber.

Openings generally comprise dimensions which ensure that the opening is entirely covered by a temperature sensor attached to the under surface of harness. In one embodiment, opening comprises a width of approximately 0.25 inches, and a length of approximately 0.75 inches.

Openings may be arranged on under surface in any configuration that allows for accurate temperature measurement. In one embodiment, openings are evenly spaced along the length of harness. In another embodiment, openings are spaced about 8 inches to about 15 inches apart.

Harness further comprises a pair of openings which are positioned on the inside surface of harness, such that openings are adjacent the inside front wall of the container. Openings are configured to receive one or more laser carriages, wherein the laser carriages house one or more laser diodes capable of emitting a fan array to form a level line on at least one of the interior sidewalls and the interior back wall of the container. Openings are provided in harness such that the light emitted by the laser diodes is directed away from a user and into the interior chamber of the container.

Openings generally comprise dimension which ensure that the opening is entirely covered by a laser carriage attached to the inside surface of harness. In one embodiment, opening comprises a width of approximately 0.375 inches, and a length of approximately 1.0 inch.

Openings may be arranged on inside surface in any configuration that achieves a continuous level line on the sidewall and back wall interior surfaces of the container. In one embodiment, openings are evenly spaced along the inside surface of harness.

Some instances of the present invention further comprise a sensor harness which comprises a wider diameter to permit easy passage of lead wires and other circuitry. Other instances provide an adjustable bracket for lowering harness deeper into the chamber, whereby to detect a colder zone within the container. Further still, some embodiments of the invention include a sensor harness comprising various cavities that allow individual sensors to be removed for calibration or cleaning.

Some embodiments of the present invention further comprise a laser module that may be easily attached and removed from the harness. This feature permits harness 1620, 1625 to be removed and cleaned without exposing the laser module and circuitry to moisture. The feature further permits easy replacement or swapping of the laser modules for a new or different laser module. In some instances, it may be desirable to use the container without a laser module. Thus, some embodiments of the present invention comprise a laser module that may be selectively added to or removed from the sensor harness.

Figure 19:
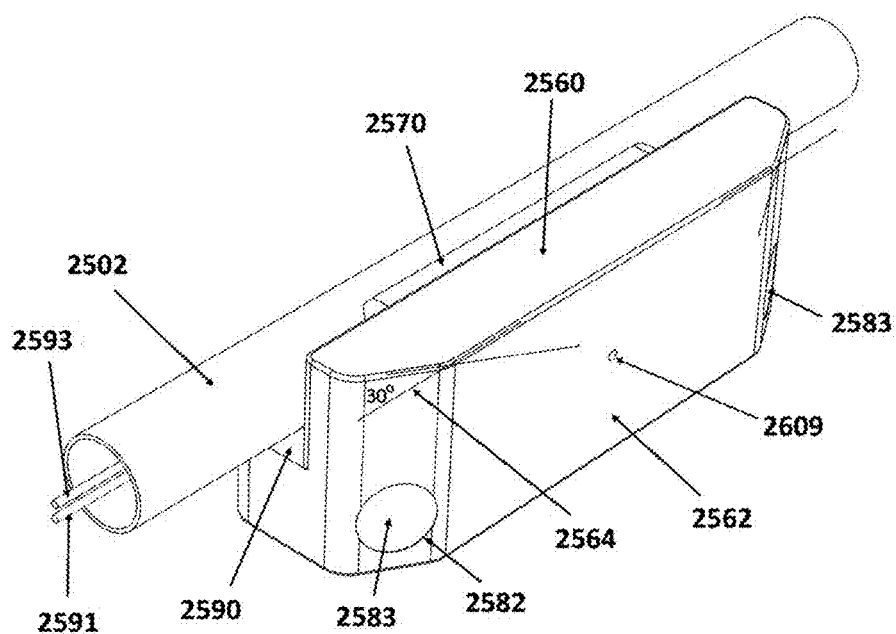
FIG. 19 provides a perspective view of a laser carriage selectively coupled to a harness via a mounting plate and harness adapter in accordance with a representative embodiment of the present invention.

FIG. 19 is a front perspective view of a laser carriage 2560 selectively coupled to harness 2502 via a harness adapter 2570. Laser carriage 2560 may comprise any size, shape, and general structure that are compatible with the features of the present invention. In one embodiment, laser carriage 2560 comprises a front surface 2562 in which is housed a pair of laser diodes 2583 which are capable of emitting a horizontal fan array to provide a level plane indicator. The laser diodes 2583 are deposited and housed in a compartment 2582 having an opening though which the laser is emitted. In some embodiments, the outer edges or corners of front surface 2562 are angled inwardly at approximately 30° with respect to the longitudinal axis 2564 of laser carriage 2560. Alternatively, in some instances front surface 2562 comprises a plane, and the corners or side edges of front surface 2562 are angled inwardly at approximately 30° with respect to the plane of front surface 2562. As such, the central axis of each compartment 2582 is angled outwardly at approximately 30° from the plane of front surface 2562. These angled surfaces, and the respective angled positions of laser diodes 2583, achieve a continuous level line emitted on the sidewall and back wall interior surfaces of the container.

In some instances, laser carriage 2560 comprises an L-shape, whereby a space 2590 is provided for accommodating placement of harness 2502. This L-shaped configuration further provides for placement of various components of within the carriage housing. In other embodiments, laser carriage 2560 comprises another shape that is compatible with the intended use of laser carriage 2560.

Figure 20:
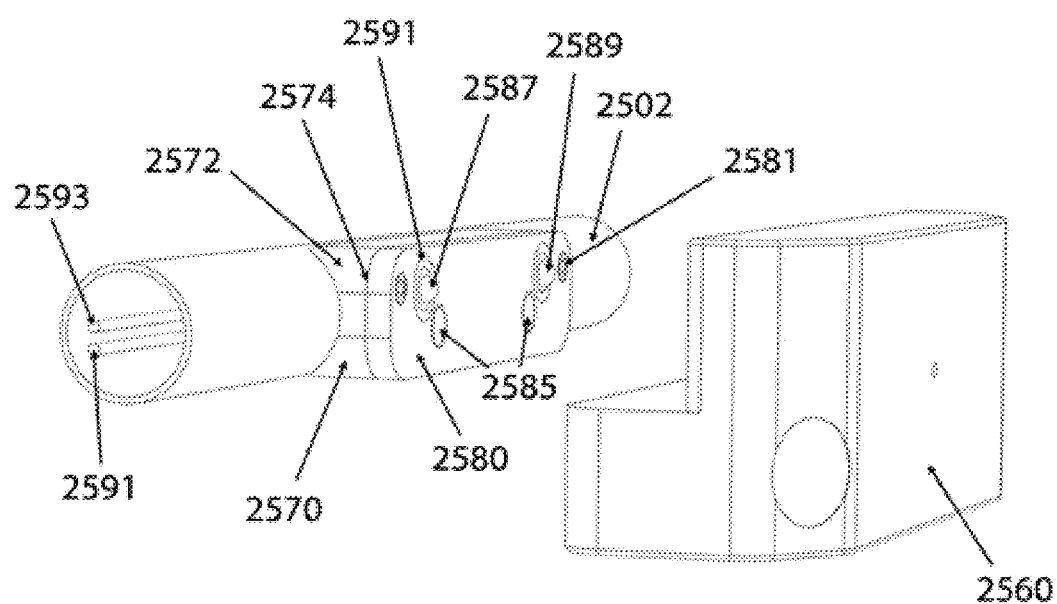
FIG. 20 provides a perspective view of a laser carriage detached from the harness, wherein the mounting plate and harness adapter remain coupled to the harness in accordance with a representative embodiment of the present invention.

Referring now to FIG. 20, laser carriage 2560 is shown separated from harness adapter 2570 and harness 2502. Harness adapter 2570 comprises a concave face 2572 configured to receive harness 2502. In some instances, harness adapter 2570 is permanently attached to harness 2502 over opening 2530 (see FIG. 21), such as by braising, welding, a temperature-resistant epoxy, or other compatible method. Harness adapter 2570 generally comprises a width that is greater than the width of opening 2530, whereby harness adapter 2570 completely surrounds and covers opening 2530.

Harness adapter 2570 further comprises a planar surface 2574 that is configured to receive carriage mounting plate 2580. Mounting plate 2580 is selectively attached to harness adapter 2570 by one or more fasteners 2581. In some instances, a fluid-tight interface is achieved between mounting plate 2580 and planer surface 2574 of harness adapter 2570.

Figure 21:
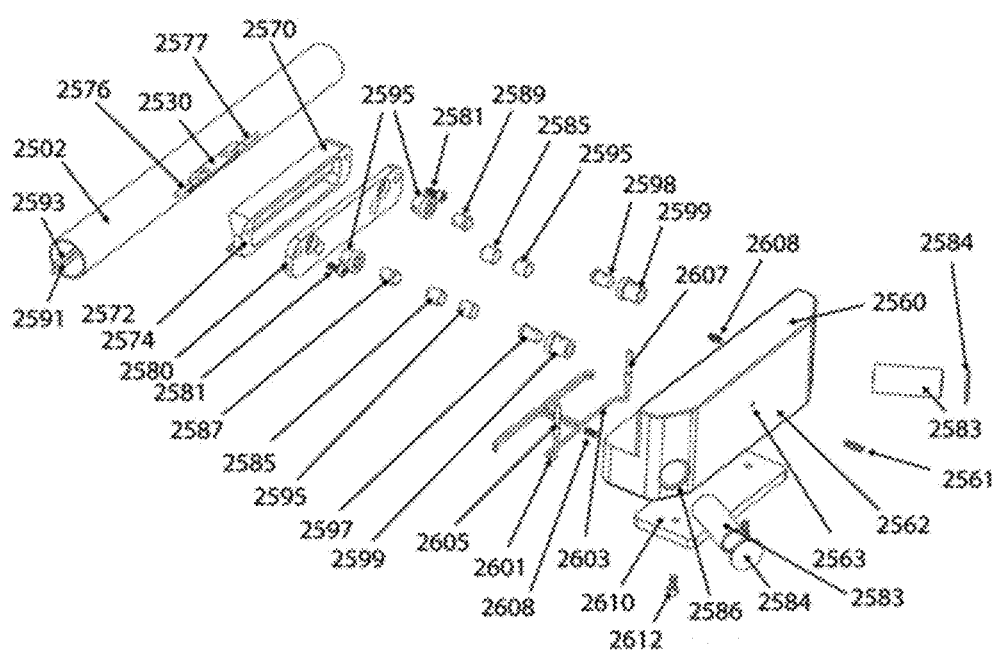
FIG. 21 provides an exploded view of a laser mounting system in accordance with a representative embodiment of the present invention.
Figure 22:
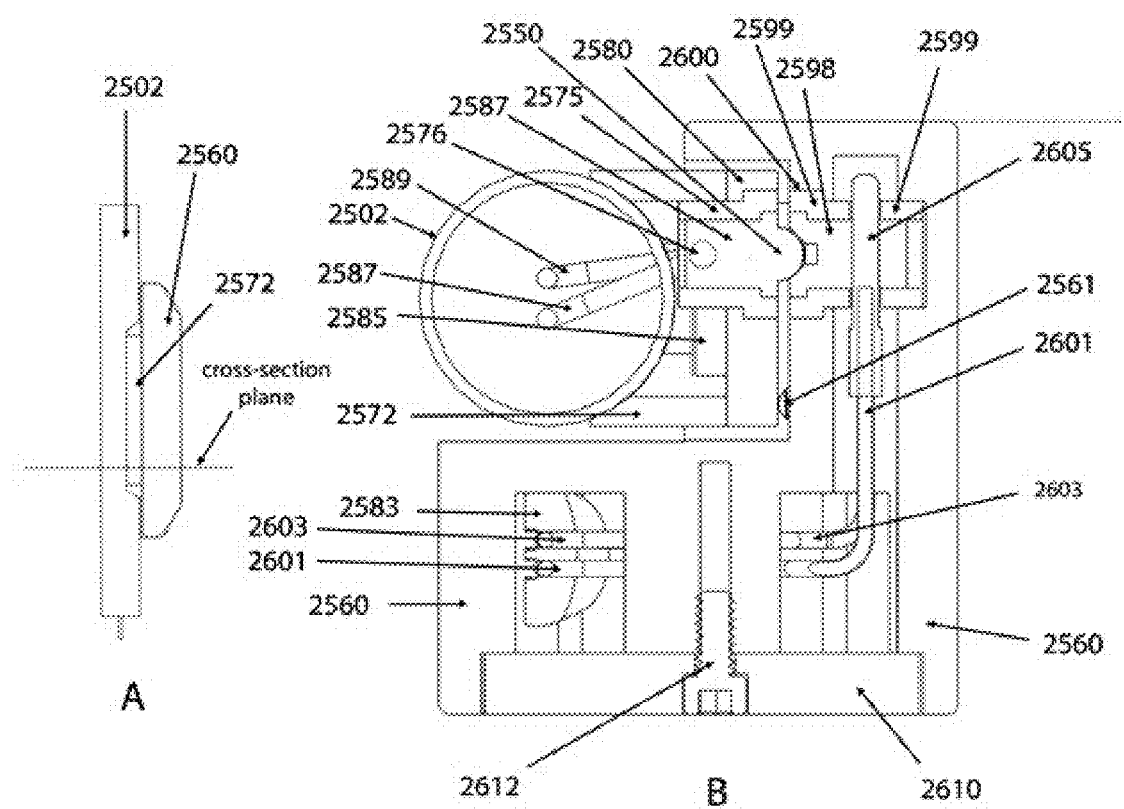
FIG. 22 is a cross-section view of a laser mounting system in accordance with a representative embodiment of the present invention.

Mounting plate 2580 further comprises mounting magnets 2585 that are embedded within mounting plate 2580 and flush with the plate's planar, front surface. Mounting magnets 2585 are positioned towards the outer edges of the plate's front surface at equal distances from a central vertical axis of the front surface. Mounting magnets 2585 are further positioned in alignment with corresponding magnets provided on laser carriage 2560, as shown in FIG. 21. Thus, laser carriage 2560 is selectively coupled to and removed from mounting plate 2580 via a magnetic interface.

Mounting plate 2580 further comprises a positive electrical terminal 2587 and a negative electrical terminal 2589 having a contact surface that extends outwardly from the plate's front surface. Each terminal is respectively coupled to positive 2591 and a negative lead wire which are fed through the hollow interior of harness 2502, as discussed above. In some embodiments, each terminal further comprises an insulator housing 2575 comprising a color or symbol to indicate the electrical polarity of the respective terminals. Electrical terminals 2587 and 2589 are securely seated into the insulated housings 2575 to insulate mounting plate 2570 from electrical current delivered to the respective electrical terminals.

Referring now to FIG. 21, an exploded view of the laser mounting assembly is shown. Harness adapter 2570 further comprises a hollow interior whereby to permit passage of lead wires 2591 and 2593 exiting from opening 2530. The electrical lead wires terminate in expanded pin jacks 2576 and 2577 for the positive wire and negative wire respectively. Mounting plate 2570 further comprises a plurality of openings, each configured to receive the insulator housings 2575, fasteners 2581, and mounting magnets 2585. Insulator housings 2575 further comprise an opening or lumen for receiving the positive and negative electrical terminals 2587 and 2589, respectively. Both the insulator housings 2575 and the electrical terminals 2587 and 2589 comprise a lateral hole recess through which the electrical wire expanded pin jacks 2576 and 2577 may be inserted to make an electrical connection by means of a friction fit. In some embodiments the electrical pin jacks are permanently secured to the electrical terminals 2587 and 2589 by means of the application of an epoxy or silicone adhesive, by solder joint, or by mechanical means such as a set screw (not shown).

Figure 24:
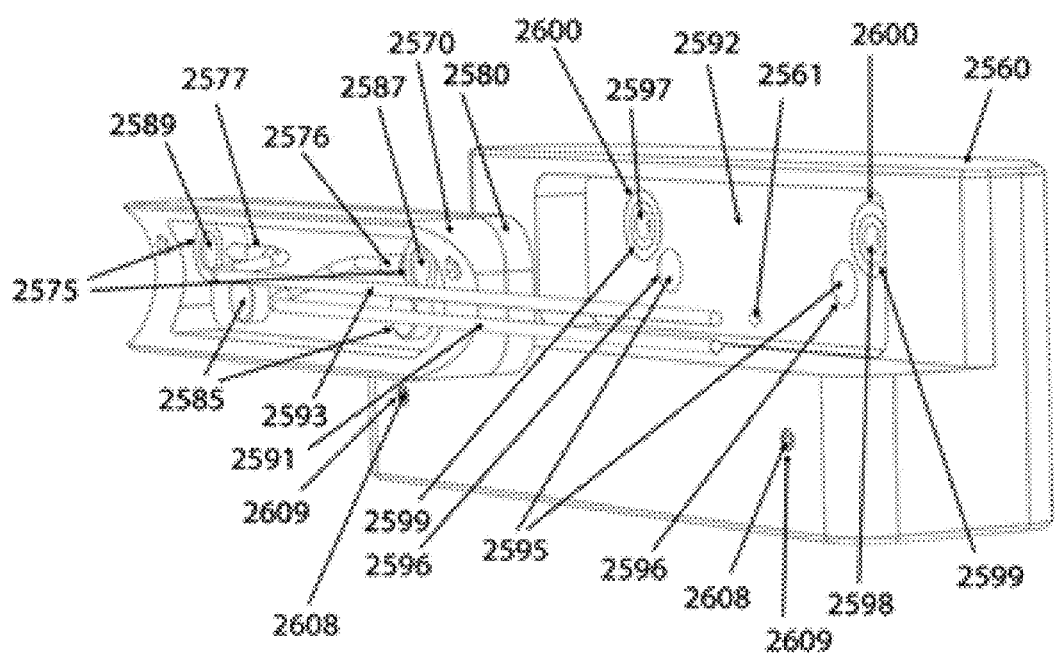
FIG. 24 is a detailed rear perspective view of a mounting plate and laser carriage in accordance with a representative embodiment of the present invention.

With continued reference to FIGS. 21 and 24, laser carriage 2560 further comprises complementary mounting magnets 2595 that are inserted into respective openings 2596 (see FIG. 24) provided on the backside of laser carriage 2560. Laser carriage also comprises complementary electrical terminals 2597 (positive) and 2598 (negative) and insulator housings 2599 which are also inserted into openings 2600 in the laser carriage 2560. In some embodiments, electrical terminals 2587 and 2589 comprise a hemispherical surface that protrudes outwardly from the front surface of mounting plate 2580. Complementary electrical terminals 2597 comprise a concave surface that is configured to receive the hemispherical surface of terminals 2587. Thus, electrical current is passed from wire leads 2591 and 2593 to electrical terminals 2597 and 2589, respectively, via the interface between the hemispherical and concave surfaces. This interface surface further acts as a pivot point between mounting plate 2580 and laser carriage 2560, whereby laser carriage 2560 may be adjusted relative to mounting plate 2580 via a set screw 2561, without disrupting the electrical current, as described below. A positive branched wire set 2601 and a negative branched wire set 2603 are housed within the laser carriage 2560 and terminate in a positive expandable pin jack 2605 and a negative expandable pin jack 2607 respectively. The pin jacks engage the receiver holes of the positive electrical terminal 2597 and negative electrical terminal 2598. The branched wire sets are in contact with and supply power to the laser diode modules 2583 through permanent solder joint attachments, and are shown separated from the diodes in FIG. 21 for spatial clarity only. Laser carriage set screws 2608 are received by the threaded hole recesses 2609 for the purpose of securing the laser diode modules 2583 in position.

With continued reference to FIGS. 21-24, in some instances the backside surface of laser carriage 2560 comprises a recess 2592 having a length, width and depth that is slightly larger than the length, width and depth of mounting plate 2580. As such, a keyed connection is provided between mounting plate 2580 and laser carriage 2560, wherein mounting plate 2580 is configured to compatibly seat within recess 2592 when laser carriage is mounted on harness 2502 via mounting plate 2580 and harness adapter 2570. A magnetic interface between mounting magnet 2585 and complementary magnet 2595 provide a secure, yet temporary connection between mounting plate 2580 and laser carriage 2560. Laser carriage 2560 may further comprise a bottom plate 2610 that is secured to laser carriage 2560 by one or more fasteners 2612. Bottom plate 2610 may be removed to gain access to compartment 2582, lead wires 2601/2603, electrical terminals 2597, and laser diodes 2580. In some embodiments, the laser modules are covered by a glass cover plate 2584 that is fixed to the laser carriage cover glass recess 2586 my means of a silicone adhesive, thereby forming a water-proof seal.

Figure 23:
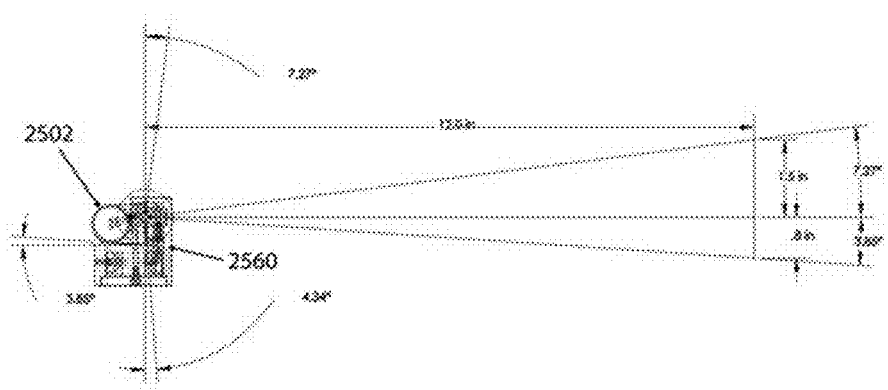
FIG. 23 is a cross-section view the laser carriage harness and adaptor showing the degree of pitch freedom of the laser carriage available by adjustment of the leveling screw, in accordance with a representative embodiment of the present invention.

In some embodiments, laser carriage 2560 further comprises a leveling set screw 2561 that engages the internal threads of hole 2563 through front surface 2562. Leveling set screw 2561 is generally centered between the positions of complementary magnets 2595 in plane that is above or beneath a plane in which the respective central axes of the magnets 2595 are aligned. As such, the respective positions of magnets 2595 and set screw 2561 form a triangular plane within recess 2592. The triangular plane may be tilted, thereby adjusting the pitch of the fan arrays emitted by laser diodes 2580, by adjusting set screw 2561. The concave and convex interface surface between electrical terminals 2581 and 2597 permit tilting between mounting plate 2580 and recess 2592 without disrupting the electrical connection. The triangular configuration of magnets 2595 and set screw 2561 further permits exclusive adjustment of the pitch of the laser carriage 2560. Referring now to FIG. 23, in some instances, leveling set screw 2561 provides a laser beam projection incidence elevation adjustment of approximately 1.5 inches up, and 0.8 inches down at a horizontal distance of 12 inches from the pivot centers 2550, located within the mounting plate electrical contacts 2587 and 2589 (see also cross-section FIG. 22).

Figure 25:
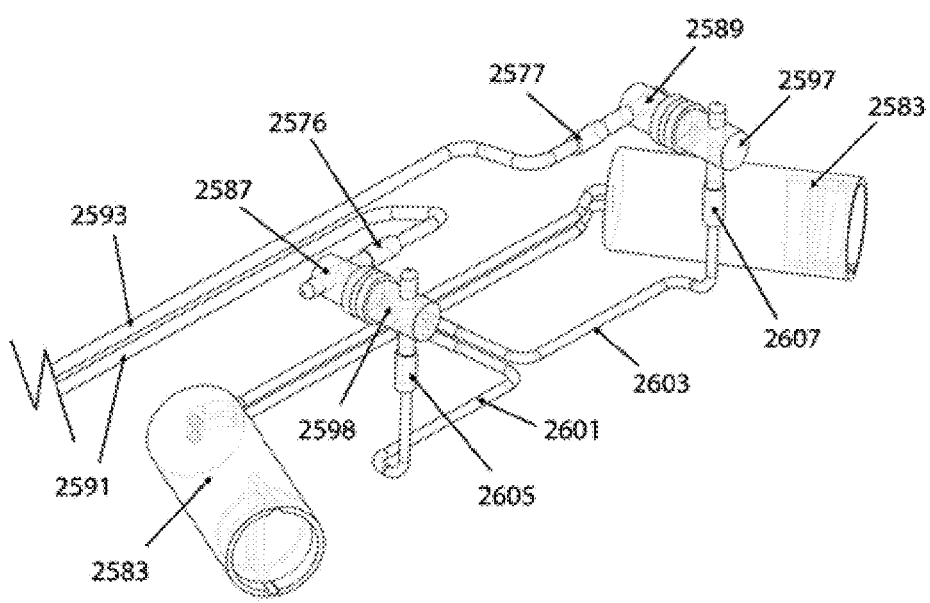
FIG. 25 is a three-dimensional perspective graphic showing the electrical pathway for the laser module power in accordance with a representative embodiment of the present invention.

Now referring to FIG. 25, isolated laser diode module 2583 poser circuit is shown. The electrical lead wires 2591 and 2593 interface with the laser mount plate terminals 2587 and 2589 which in-turn are in contact with carriage terminals 2598 and 2587 respectively. The carriage jack pin contacts 2605 and 2607 are in contact with the carriage terminals 2598 and 2597 respectively. Positive electrical lead 2601 is joined to jack pin 2605 and negative electrical lead 2603 is joined to jack in 2607 and both electrical leads branch to supply the power to the laser diodes 2583 which are wired in parallel.

ILLUSTRATIVE EXAMPLES

Example 1

Central Vial Transfer and Packaging Station

A central vial transfer and packaging station is provided which comprises a stationary system that provides an ultra-cold work area for transferring finished product vials from a sample tray (for example, a 40-count sample tray or storage box) to a product cartons (for example, a 20-count product tray or box). The station comprises a chamber made of cross-linked closed-cell HDPE foam and houses a nitrogen boiler, sensors, lasers, and a device harness (i.e., a structure for supporting the sensors and lasers). The harness is capable of supporting six Resistance Temperature Detectors (RTDs) (for example, Pyromation RTDs), four Channel Expansion Module sensors (CEMSs), and one or more lasers which provide guidelines designating the ultra-cold work zone. In some instances, the RTDs and CEMSs are connected to a display and/or a computer system by a wire lead. In other instance, the RTDs and CEMSs are connected to a display and/or computer system by a wireless connection.

When the system power is set to the ON position, the CEMSs and RTDs begin real-time temperature monitoring and recording. When laser power is set to the ON position, the lasers illuminate a linear boarder on the inner wall of the chamber to guide operator on the upper limit of the ultra-cold work zone. The chamber is placed on a table at a working height (for example 40° from ground level to the top of the chamber).

The chamber further includes a Videographic Recorder and Display (for example, an ABB ScreenMaster 1000 (SM1000)), and stack tower lights with audio and visual alarms to indicate a temperature fault. In some instances, solid state relays (SSRs) are controlled by digital signals sent from the Videographic Recorder and are used to activate higher voltage needed for the audible and visual alarms of the stack tower lights.

For portable units, the chamber further includes a battery box containing two 12V batteries 2460. In some instances, the battery box 2462 or enclosure is built according to NEMA 4X specifications. In one embodiment, a battery box 2462 is provided having a height of approximately 9.0 inches, a width of approximately 12.0 inches, and a depth of approximately 7.0 inches.

Portable units may further include a 24 VDC locking receptacle for recharging the batteries. For example, a 15 Amp, 125 volt, NEMA ML1P, 2P flanged inlet locking receptacle is provided which comprises a twist mini lock feature and is operably connected to the batteries 2460. The receptacle is rugged, resists impact, sunlight, chemicals and rough use. The battery charging cord further comprise a 24 VDC locking receptacle. In particular, the charging cord include a 15 Amp, 125 Volt, NEMA ML1R, 2P locking connector, mounted on the battery charger cord to provide a secure connection during battery charging operation. These receptacles are keyed to only accept NEMA ML1-C compatible plugs, thereby preventing incompatible charging systems.

Portable and/or non-portable units may additionally include a power supply and inverter for use with 120 and/or 220 volt receptacles. In some instances, 12V batteries or AC receptacle power source is reduced to a 3.3 volt power source by means of a DC-DC or AC-DC converter, whereby the 3.3 volts is used to operate the laser.

The station may further include a front panel comprising a plurality of switches and other controls by which the station is operated. In some instances the front panel is located above the Videographic Recorder. The front panel includes a system power switch which controls the "ON" and "OFF" status of the station. This switch is connected to the power source of the station to allow the user to selectively control and power all of the electrical components of the station, with the exception of the lasers. The front panel further comprises a laser power switch that is dedicated solely to the operation of the lasers. Thus, a user may selectively operate the station with or without the lasers.

The RTDs are attached to the device harness and are operably connected to the Videographic Recorder to monitor and record temperature changes inside the working zone. The working zone height is marked by a spread-beam produced by the laser, wherein the spread-beam marks the working space boundary. The stack lights tower with audio and visual alarms provides the user with an audible and/or visual warning when the temperature within the chamber reaches a temperature limit set on the Videographic Recorder.

In some instances, a stack lights tower is provided having three operating levels, namely: 1) a green light zone which indicates that the operating conditions of the chamber are within a set specification; 2) a yellow light zone which indicates that the operating conditions of the chamber have deviated from a set specification; and 3) a red light zone which indicates that the operating conditions of the chamber are outside of an acceptable range based on a set specification, thereby requiring the user to take immediate action. Generally, the stack lights tower is coupled to an outer surface of the chamber, or a cart holding the chamber, such that the lights are clearly visible to the user. In some instances, the stack lights tower is mounted on the back of a cart that holds the chamber, wherein the tower is well within the view of the user.

Example 2

Multiple Module Transfer and Packaging Station

A multiple module transfer and packaging station is provided which comprises a plurality of stationary vial transfer and packaging stations or modules that are interconnected to provide a single, complete product packaging operation. A multiple module transfer and packaging station is further provided which comprises a plurality of mobile vial transfer and packaging stations or modules that are interconnected to provide a single and mobile complete product packaging operation. Further still, a multiple module transfer and packaging station is provided which comprises a plurality of mobile and stationary vial transfer and packaging stations or modules that are either interconnected and/or used in concert to provide a single, complete product packaging operation. In some instances, a complete product packaging operation comprises four vial transfer and packaging stations.

Each of the chambers of the mobile and/or stationary modules has an opening defined by a rim. Generally, the rims of the module chambers are set at a uniform working height above the floor or ground on which the modules are supported. In some instances the rims are set at a working height from approximately 28 inches to approximately 50 inches. In other instances the rims are set at a working height from approximately 36 inches to approximately 44 inches. In one embodiment, the rims are set at a working height of approximately 40 inches.

The chambers are comprised of a highly durable HDPE foam material. The HDPE foam provides a highly insulative environment to maintain a desired working temperature within the chamber. In some instances, the chamber comprises four sidewalls and a base which define the chamber. The sidewalls and base of the device comprises a wall thickness that provides sufficient insulation to prevent transfer of heat to the outer surface of the chamber. In some instances, the chamber comprises a wall thickness from approximately 2 inches to 8 inches. In other embodiments the chamber comprises a wall thickness of approximately 6 inches. Thus, the insulative properties of the HDPE foam, when provided at the desired wall thickness, optimally maintain a desired working temperature within the chamber, and prevent burn injuries to the user when the outer surface of the chamber is contacted.

Example 3

Chest Freezer Tower Rack Adaptor

A chest freezer tower rack adapter is provided that is designed to be placed on the floor of the chamber of a vial transfer and packaging station. The adapter comprises a thermoconductive material, such as anodized aluminum, and includes a plurality of protrusions that are spaced to permit precise insertion of each protrusion into an individual opening in the bottom of a chest freezer rack when the chest freezer rack is laid horizontally on top of the rack adapter. The individual openings are located in the bottom surface of the sample rack. The individual openings have a diameter or cross-section that permits easy insertion of the protrusions therethrough, yet prevents passage of a sample vial.

The rack adapter is placed on the floor of the chamber and permitted to equilibrate to the desired working temperature. A chest freezer rack is then placed over the rack adapter in a horizontal orientation such that the protrusions are lined up with, and inserted within the individual openings in the bottom of the sample rack. As the freezer rack descends over the rack adapter, the protrusions contact sample trays stored in the chest freezer rack, thereby lifting the sample trays out of their individual compartments and into an elevated position. The user may then easily access and grip the sample trays for easy transfer from the freezer rack to the chamber.

Example 4

Vial Picking Hand Tool

A vial picking hand tool is provided that is designed to permit a user to pick up and remove a single vial from a sample tray and transfer the vial to an empty product carton prepositioned in a product tray. The hand tool comprises long handles that allow the user to avoid inserting hands or arms into the ultra-cold working environment, thereby providing protection and comfort to the user.

Example 5

Product Carton Closing Hand Tool

A product carton closing hand tool is provided that is designed to permit a user to close the flaps and lid of a product carton after a product vial is inserted into the carton. The hand tool comprises long handles that allow the user to avoid inserting hands or arms into the ultra-cold working environment, thereby providing protection and comfort to the user.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

I claim:
1. A system comprising:
    a container comprising one or more sides and a floor with an open-top surface forming an interior chamber wherein a liquid-tight metal tank, comprising at least one opening at the open-top surface of the liquid-tight metal tank capable of exhausting gas directly into the chamber is mounted on or in close proximity to an interior side wall; and
    a laser mounting system on the container, the laser mounting system comprising:
        a laser carriage comprising a laser diode electrically connected to a first electrical terminal, and further comprising a first magnet,
        a mounting plate comprising a second electrical terminal and a second magnet, the second electrical terminal and second magnet being positioned to align with the first electrical terminal and the first magnet when laser carriage is coupled to the mounting plate,
        a harness adapter having a first surface for receiving an outer surface of a sensor harness and an opposing surface for receiving the mounting plate, the harness adapter being interposed between the harness and the mounting plate, and
        a lead wire coupled to the second electrical terminal.
2. The system of claim 1 wherein the container comprises a material with a thermal conductivity less than 0.2 watts per meter kelvin.
3. The system of claim 2, wherein the material comprises cross-linked polyethylene foam, urethane foam, styrene foam, polyvinyl foam, or a polymer blend foam.

4. The system of claim 1, wherein the liquid-tight metal tank comprises steel, stainless steel, copper, a copper alloy, aluminum, or an aluminum alloy.

5. The system of claim 1 wherein the liquid-tight metal tank comprises one or more liquid-filling ports, sensor mounts, and sensor housings.

6. The system of claim 1 in which the chamber temperature may be regulated to a predetermined temperature range.

7. The system of claim 5 wherein the system comprises a liquid level sensor or a temperature sensor or both.

8. The system of claim 7 to which is attached piping, tubing or gravity chutes to direct liquid into the liquid-tight metal tank.

9. The system of claim 8 to which is attached a microprocessor receiving electric signals from a liquid level sensor or from temperature sensor or both, and delivering an electric signal to a liquid delivery regulator.

10. The system of claim 9 wherein the chamber comprises one or more temperature sensors to monitor the interior gas temperature.

11. The system of claim 10 wherein the temperature sensor is a thermocouple or an RTD sensor.

12. The system of claim 1, further comprising an attached external liquid refrigerant reservoir, wherein the attached external liquid refrigerant reservoir is pressurized by an electric current passed through a resistance coil that is submerged in a liquid refrigerant, or wherein the liquid refrigerant is moved through an action of a mechanical pump.

13. The system of claim 12 wherein a liquid nitrogen delivery system comprises a covered gravity chute.

14. The system of claim 1 wherein
the liquid-tight metal tank comprises a plurality of rims to limit spillage, and
the liquid-tight metal tank is positioned in the interior chamber so that a lowest rim of the plurality of rims of the at least one opening of the liquid-tight metal tank no lower than seventy-five percent of a height of the interior chamber.

15. The system of claim 14 wherein the liquid-tight metal tank has one or more level top edges whereby overflow of cold gas from the liquid-tight metal tank will fall evenly down a tank face beneath the level to edge.

16. The system of claim 15 wherein the liquid-tight metal tank is constructed with a long dimension greater than fifty percent of a length of a chamber wall on which it is affixed.

17. The system of claim 14 wherein an interior of the liquid-tight metal tank comprises removable or permanently attached baffles, screens, or porous materials that may suppress or restrict liquid movement in the interior of the liquid-tight tank.

18. The system of claim 1 wherein a deck covers a portion of the interior chamber.

19. The system of claim 18 whereupon one or more instruments, panel interfaces, control features, sensors, electronics, data recorders, wireless linkages, power connections, and liquid nitrogen delivery ports and linkages is affixed to said deck.

20. The system of claim 1, wherein the laser diode comprises a pair of laser diodes.

21. The system of claim 20, wherein a front surface of the laser carriage comprises a plane, and wherein a side corner edge of the front surface is angled inwardly in the range of 10°-50°, and wherein a central axis of the laser diode is angled at approximately 30° relative to the plane of the front surface.

22. The system of claim 21, wherein the laser diode comprises a first laser diode positioned on a first angled corner of the front surface, and a second laser diode positioned on a second angled corner of the front surface, wherein the first angled corner is opposite the second angled corner on the front surface.

23. The system of claim 22, wherein an angle between a central axis of the first laser diode and a central axis of the second laser diode is in the range of 20°-100°.

24. The system of claim 23, wherein the laser carriage is selectively removable from the mounting plate.

25. The system of claim 24, wherein the harness adapter is permanently attached to the harness.

26. The system of claim 25, wherein the mounting plate is removably coupled to the harness adapter via a fastener.

27. The system of claim 26, further comprising a magnetic interface between the mounting plate and the laser carriage.

28. The system of claim 27, further comprising a keyed connection between the mounting plate and the laser carriage.

29. A method for creating a container with an open-top cavity filled with low temperature gas wherein a portion of the low temperature gas is at a temperature below −80 degrees Celsius comprising:
providing a laser mounting system, wherein the laser mounting system is on the container, the laser mounting system comprising:
a laser carriage comprising a laser diode electrically connected to a first electrical terminal, and further comprising a first magnet,
a mounting plate comprising a second electrical terminal and a second magnet, the second electrical terminal and second magnet being positioned to align with the first electrical terminal and the first magnet when laser carriage is coupled to the mounting plate, and
a harness adapter having a first surface for receiving an outer surface of a sensor harness and an opposing surface for receiving the mounting plate, the harness adapter being interposed between the harness and the mounting plate, and a lead wire coupled to the second electrical terminal;
evaporating liquid nitrogen within a metal tank affixed to a container wall to form a nitrogen vapor and exhausting the nitrogen vapor directly into the container cavity.

30. The method of claim 29 wherein the low temperature gas temperature is regulated by control of a level of liquid nitrogen contained within the metal tank.

31. The method of claim 29, further comprising mixing the low temperature gas within the container cavity at an increased rate relative to a rate of mixing the low temperature gas within the container cavity obtained when the liquid nitrogen is contained in the metal tank resting on a floor of a chamber of the container.

32. The method of claim 31 wherein the uniformity of the gas temperature within the container cavity is increased by the mixing effect of the liquid nitrogen from the metal tank.

33. The method of claim 29 wherein the chamber temperature is at a reduced temperature compared to the metal tank when resting on a floor of a chamber of the container.

34. The method of claim 29 wherein a flow of the low temperature gas from the metal tank increases exposure of a warmer cavity gas to a surface of the liquid nitrogen.

35. The method of claim 29, further comprising exposing a chamber of the container to the low temperature gas by flowing the nitrogen vapor downward in a direction of a gravitational field.

* * * * *

UNITED STATES PATENT AND TRADEMARK OFFICE
CERTIFICATE OF CORRECTION

PATENT NO. : 10,531,656 B2
APPLICATION NO. : 14/895488
DATED : January 14, 2020
INVENTOR(S) : Brian Schryver Page 1 of 1

It is certified that error appears in the above-identified patent and that said Letters Patent is hereby corrected as shown below:

In the Claims

Column 37, Line 37, Claim 14: replace "the at least one opening of the liquid-tight metal tank no" with – "an opening of the liquid-tight metal tank is no".
Column 37, Line 43, Claim 15: replace "down a tank face beneath the level to edge" with – "down a face of the liquid-tight metal tank beneath the level top edge".

Signed and Sealed this
Twenty-fourth Day of March, 2020

Andrei Iancu
*Director of the United States Patent and Trademark Office*